(12) United States Patent
Schraga

(10) Patent No.: US 10,092,230 B2
(45) Date of Patent: Oct. 9, 2018

(54) FLUID COLLECTION/INJECTION DEVICE HAVING SAFETY NEEDLE ASSEMBLY/COVER AND SAFETY SYSTEM AND METHOD

(75) Inventor: Steven Schraga, Surfside, FL (US)

(73) Assignee: STAT MEDICAL DEVICES, INC., North Miami Beach, FL (US)

( * ) Notice: Subject to any disclaimer, the term of this patent is extended or adjusted under 35 U.S.C. 154(b) by 1712 days.

(21) Appl. No.: 13/458,468

(22) Filed: Apr. 27, 2012

(65) Prior Publication Data

US 2012/0277628 A1 Nov. 1, 2012

Related U.S. Application Data

(60) Provisional application No. 61/480,787, filed on Apr. 29, 2011.

(51) Int. Cl.
| | | |
|---|---|---|
| A61B 5/153 | (2006.01) | |
| A61M 5/32 | (2006.01) | |
| A61B 5/15 | (2006.01) | |
| A61B 5/154 | (2006.01) | |

(52) U.S. Cl.
CPC .... *A61B 5/150587* (2013.01); *A61B 5/15003* (2013.01); *A61B 5/154* (2013.01); *A61B 5/150389* (2013.01); *A61B 5/150496* (2013.01); *A61B 5/150572* (2013.01); *A61B 5/150671* (2013.01); *A61B 5/150717* (2013.01); *A61B 5/150732* (2013.01); *A61M 5/3216* (2013.01); *A61M 2005/3206* (2013.01); *A61M 2005/3217* (2013.01)

(58) Field of Classification Search
CPC .......... A61B 5/15003; A61B 5/150389; A61B 5/1411; A61B 5/1438; A61B 5/150732; A61B 5/154; A61B 5/1405
USPC ........................................................ 600/576
See application file for complete search history.

(56) References Cited

U.S. PATENT DOCUMENTS

| | | |
|---|---|---|
| 4,490,142 A | 12/1984 | Silvern |
| 4,813,426 A | 3/1989 | Haber et al. |
| 4,822,343 A | 4/1989 | Beiser |
| 4,838,863 A | 6/1989 | Allard et al. |
| 4,904,244 A | 2/1990 | Harsh et al. |
| 4,907,600 A | 3/1990 | Spencer |
| 4,915,702 A | 4/1990 | Haber |
| 4,984,580 A | 1/1991 | Wanamaker |
| 4,993,426 A | 2/1991 | Spencer |
| 4,994,034 A | 2/1991 | Botich et al. |
| 5,114,410 A | 5/1992 | Caralt |

(Continued)

*Primary Examiner* — Sean Dougherty
*Assistant Examiner* — Patrick Fernandes
(74) *Attorney, Agent, or Firm* — Thomas | Horstemeyer, LLP

(57) ABSTRACT

Fluid collection/injection device comprises a body having a front end, a back end, and a main hollow section arranged between the front and back ends and a needle hub securing section arranged on the front end and being structured and arranged to receive therein a needle member. The fluid collection/injection device is structured and arranged to utilize at least an operational mode, an operational mode, and a post-use mode. In the installation mode, the needle member is coupled to the body via the needle hub securing section. In the operational mode, fluid passes through the needle member and into or out of a receptacle inserted into the main hollow section.

22 Claims, 27 Drawing Sheets

(56) References Cited

U.S. PATENT DOCUMENTS

| | | |
|---|---|---|
| 5,117,837 A | 6/1992 | Wanamaker et al. |
| 5,180,370 A | 1/1993 | Gillespie |
| 5,385,551 A | 1/1995 | Shaw |
| 5,407,436 A | 4/1995 | Toft et al. |
| 5,423,758 A | 6/1995 | Shaw |
| 5,578,011 A | 11/1996 | Shaw |
| 5,616,136 A | 4/1997 | Shillington et al. |
| 5,632,733 A | 5/1997 | Shaw |
| 5,637,101 A | 6/1997 | Shillington et al. |
| 5,755,673 A | 5/1998 | Kinsey |
| 5,797,490 A | 8/1998 | Fujii et al. |
| 5,810,775 A | 9/1998 | Shaw |
| 6,015,438 A | 1/2000 | Shaw |
| 6,024,710 A | 2/2000 | Miller |
| 6,171,284 B1 | 1/2001 | Kao et al. |
| 6,432,087 B1 | 8/2002 | Hoeck et al. |
| 6,551,288 B2 * | 4/2003 | Payne et al. ............ 604/263 |
| 6,572,565 B2 | 6/2003 | Daley et al. |
| 6,932,793 B1 | 8/2005 | Marshall et al. |
| RE38,964 E | 1/2006 | Shillington |
| RE39,107 E | 5/2006 | Shaw |
| 7,163,526 B2 * | 1/2007 | Leong et al. ......... 604/168.01 |
| 7,521,022 B2 | 4/2009 | Konrad |
| 7,533,293 B2 | 6/2009 | Jensen et al. |
| 2008/0262421 A1 | 10/2008 | Schraga |
| 2010/0286558 A1 | 11/2010 | Schraga |
| 2011/0160613 A1 | 6/2011 | Schraga |

* cited by examiner

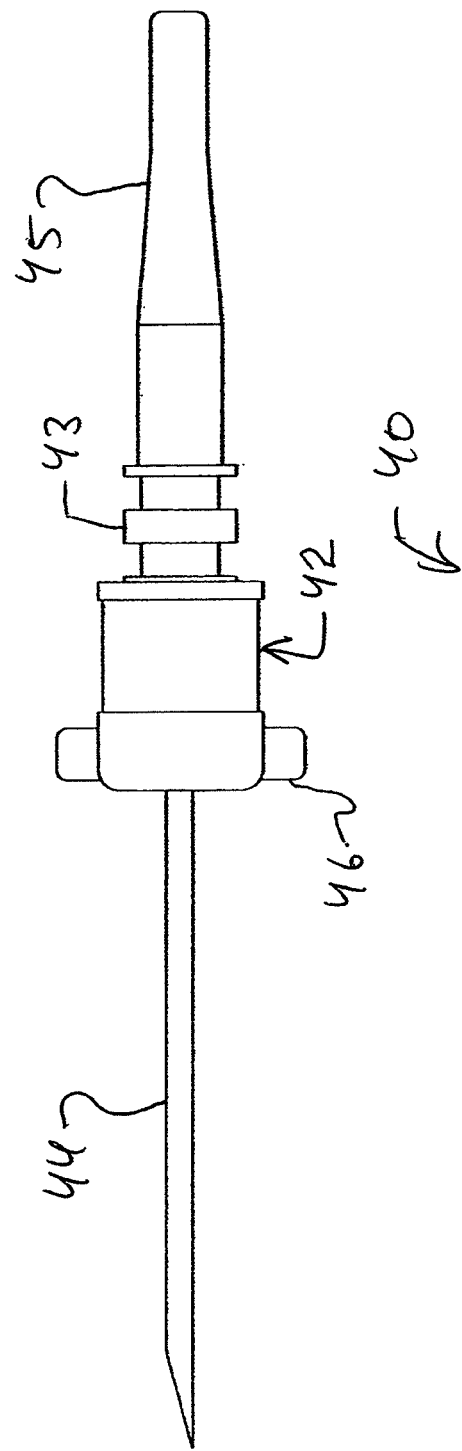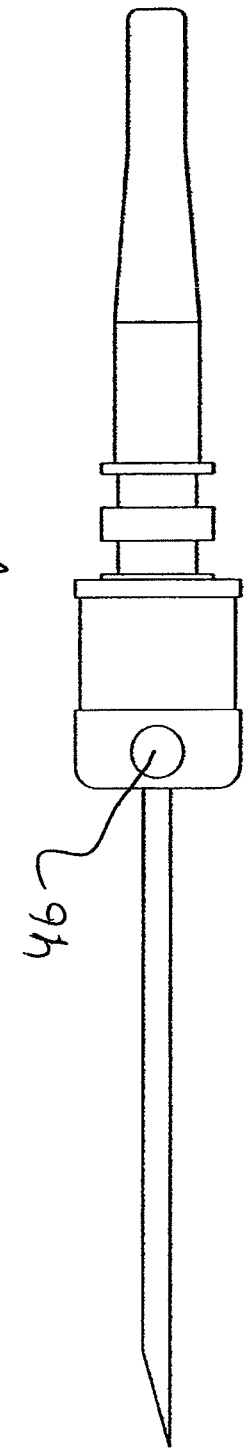

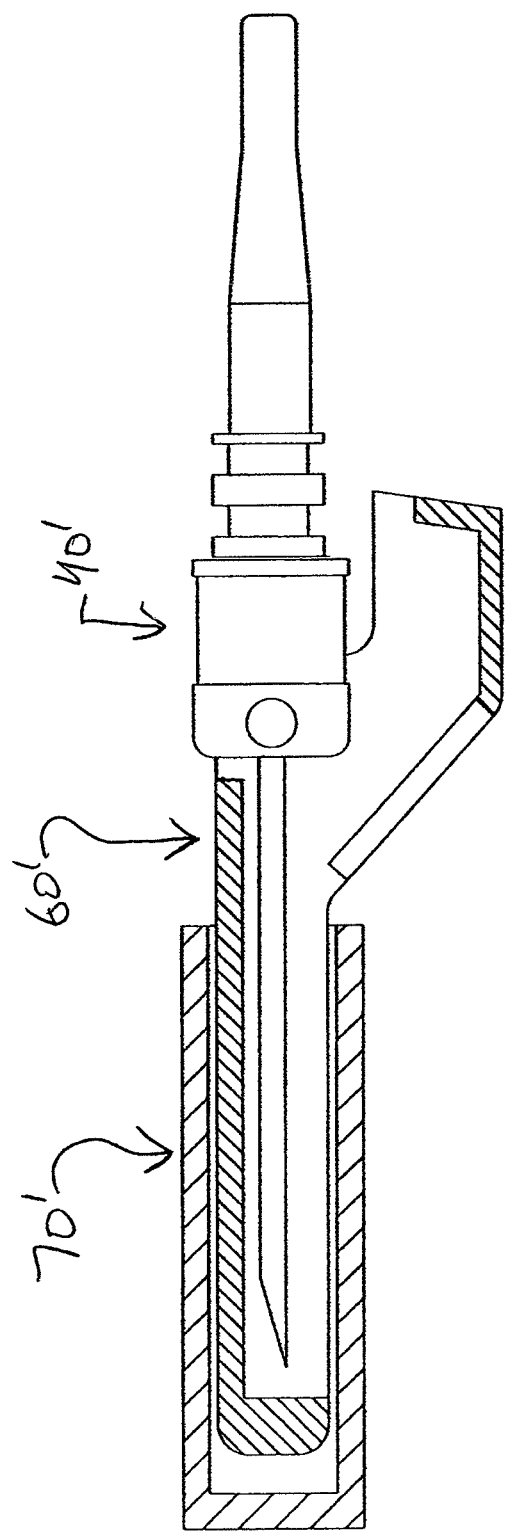

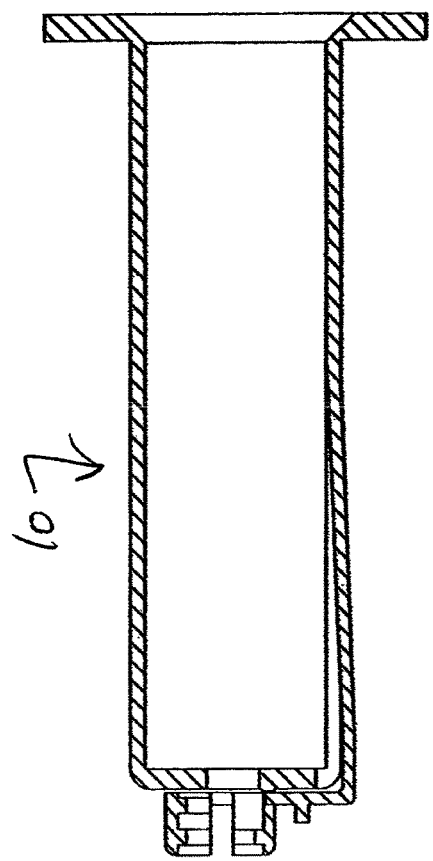
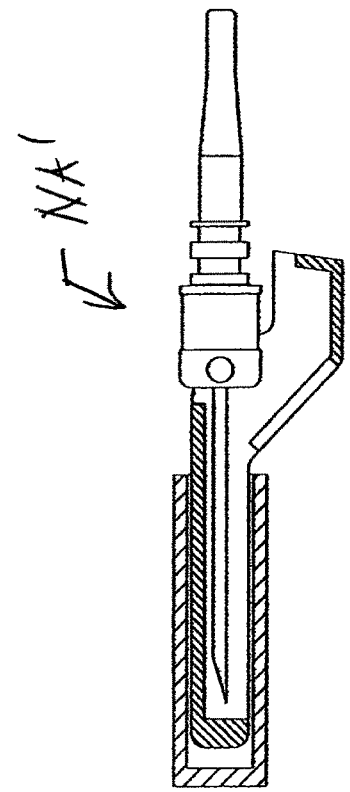
Fig. 16

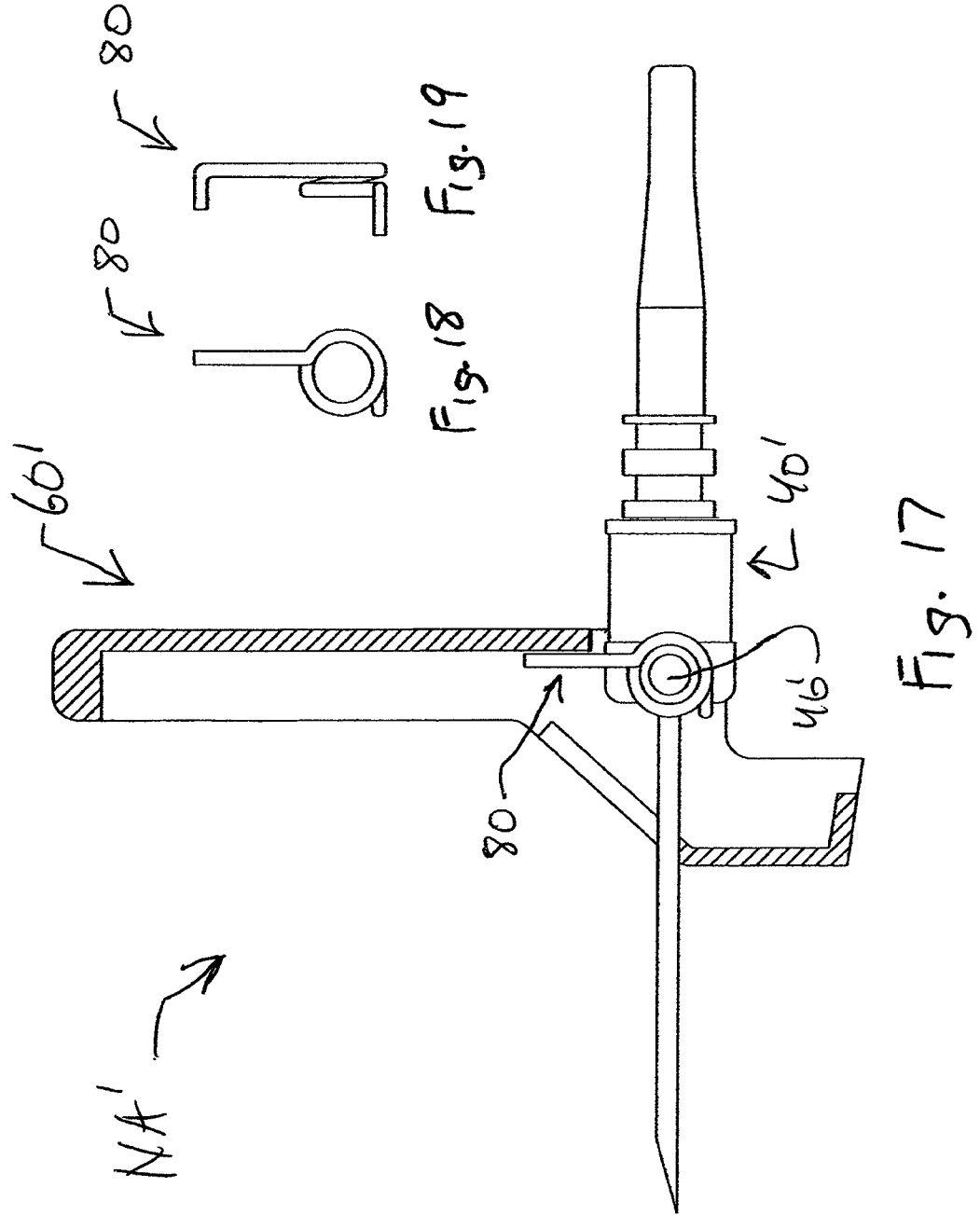

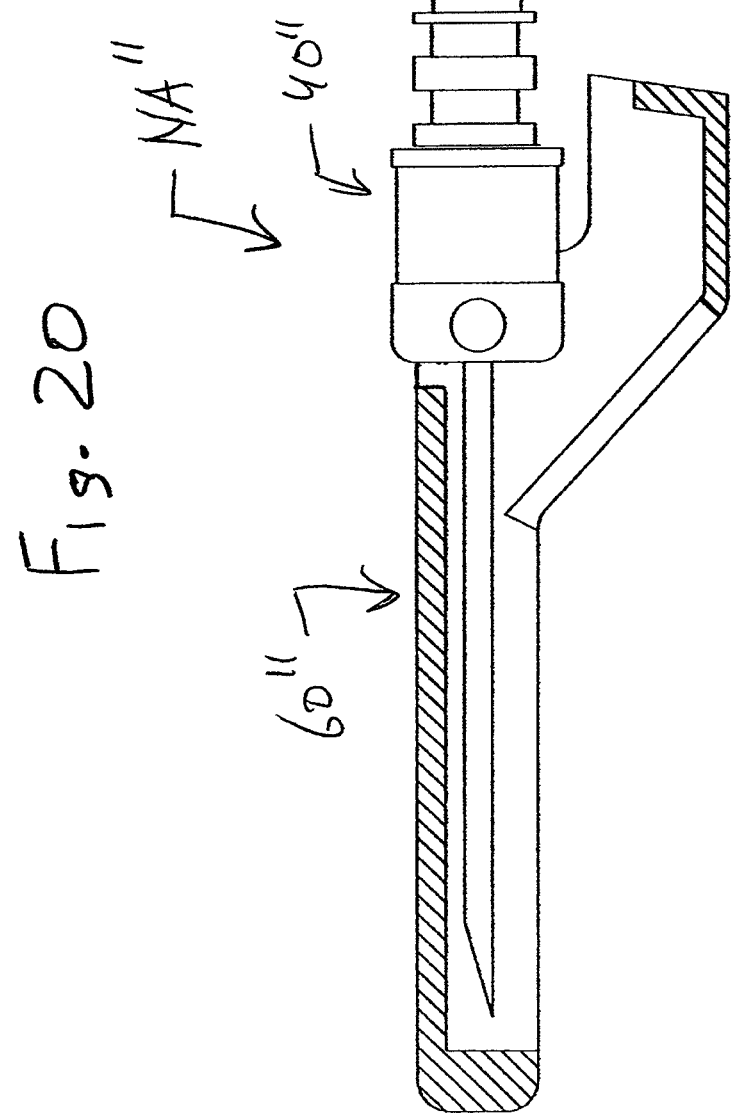

FLUID COLLECTION/INJECTION DEVICE HAVING SAFETY NEEDLE ASSEMBLY/COVER AND SAFETY SYSTEM AND METHOD

CROSS-REFERENCE TO RELATED APPLICATIONS

The instant application is a US non-provisional Application that is based on and claims the benefit of U.S. provisional application No. 61/480,787, filed Apr. 29, 2011, the disclosure of which is hereby expressly incorporated by reference hereto in its entirety.

BACKGROUND OF THE INVENTION

1. Field of the Invention

This invention relates generally to devices used to collect fluid samples from and/or inject fluids into patients. More specifically, this invention relates to a device which utilizes a holder having a double-ended needle that can be released or removed from the holder in a more safe and easy manner. The device can be a single-use device. The invention also relates to a method of collecting a fluid sample with the device as well as a method of making the device. The invention also relates to a blood sample collection device that is less costly to produce, is safer to use, and/or is easier to manufacture.

2. Discussion of Background Information

Prevention of needle sticks is of paramount concern in the healthcare industry because of serious and deadly risk factors associated with AIDS and other serious communicable diseases. Typical blood collection devices utilize a needle inserted into a patient's vein so as to draw blood through the needle into an associated separate collection reservoir. Accidental needle sticks from previously used needles can occur during the fluid withdrawing process and subsequent handling and disposal operation. Until such used medical devices are destroyed, they remain a risk to those handling them.

Devices used for blood sampling are well know and include a collection device sold under the trademark Vacutainer® by Becton Dickinson Corporation. This device has a tubular syringe-like body with a needle in the front end, part of which extends back into a tubular syringe-like shell. Part of the needle extends externally for punching the skin. An evacuated collection tube with a rubber stopper is placed into the open back of the syringe-like shell with the rubber stopper against the internal end of the needle. After the skin is punctured, the collection tube is pushed forward to cause the needle to enter the evacuated tube. Vacuum helps draw blood into the collecting tube. When a sufficient sample has been obtained, the collecting tube and the stopper are simply withdrawn from the tubular shell and sent to the laboratory. This particular device has a permanently extended needle and an opening in the back for the collection tube which remains open after the collection tube is removed, leaving small quantities of blood and an internally exposed needle.

Medical devices which are used for collecting fluid samples from patients which have quick release needle systems are also known. Such devices include: U.S. Pat. No. 5,797,490 to FUJI et al; U.S. Pat. No. 5,755,673 to KINSEY; U.S. Pat. No. 4,822,343 to BEISER; U.S. Pat. No. 4,984,580 WANAMAKER; U.S. Re. 38,964 to SHILLINGTON; U.S. Pat. No. 5,616,136 to SHILLINGTON et al.; U.S. Pat. No. 5,637,101 to SHILLINGTON; U.S. Pat. No. 5,117,837 to WANAMAKER et al.; U.S. Pat. No. 4,907,600 to SPENCER; U.S. Pat. No. 4,993,426 to SPENCER; U.S. Pat. No. 4,904,244 to HARSH et al.; U.S. Pat. No. 4,490,142 to SILVERN. The disclosures of each of these documents is expressly incorporated by reference herein in their entireties.

The invention aims to improve devices of the type described above by making a fluid collection holder which is easier to make and use. The device is also believed to be as safe or safer to use and/or dispose-of than the above-noted devices.

SUMMARY OF THE INVENTION

According to one non-limiting aspect of the invention there is provided a fluid collection/injection device including one or more features shown herein in combination with one or more devices disclosed above. In embodiments, there is provided a fluid collection/injection device including one or more features shown herein in combination with one or more devices disclosed in U.S. Ser. No. 12/755,917 filed on Apr. 7, 2010 (US 2010/0286558), and/or U.S. Ser. No. 12/974,908 filed on Dec. 21, 2010 (US 2011/0160613) and/or U.S. Ser. No. 11/738,240 filed on Apr. 20, 2007 (US 2008/0262421). The disclosure of each of these documents is expressly incorporated by reference herein in their entireties.

According to one non-limiting embodiment of the invention, there is provided a fluid collection/injection device comprising a body having a front end, a back end, and a main hollow section arranged between the front and back ends and a needle hub securing section arranged on the front end and being structured and arranged to receive therein a needle member. The fluid collection/injection device is structured and arranged to utilize at least an operational mode, an operational mode, and a post-use mode. In the installation mode, the needle member is coupled to the body via the needle hub securing section. In the operational mode, fluid passes through the needle member and into or out of a receptacle inserted into the main hollow section. In the post-use mode, a safety cover at least one of: prevents re-use of the fluid collection/injection device; prevents removal of the needle member from the fluid collection/injection device; prevents removal of the needle member from the needle hub securing section; activates release of the needle member from the body such that when the safety cover is in a position covering a needle of the needle member, the needle member can fall out of the needle hub securing section; activates release of the needle member from the body such that when the safety cover is in a position covering a needle of the needle member, the needle member is no longer securely retained to the needle hub securing section; releases a securing engagement between the needle member and the needle hub securing section; unlocks a locking connection between the needle member and the needle hub securing section; and moves a mechanism arranged in an area of the needle hub securing section which releases a connection between the needle member and the needle hub securing section.

According to one non-limiting embodiment of the invention, the body is one of generally cylindrical and generally tubular.

According to one non-limiting embodiment of the invention, the needle hub securing section comprises a fixed part and a movable part.

According to one non-limiting embodiment of the invention, the fixed part is integrally formed with the front end and the movable part is arranged on a member that has one end which is one of: fixed to a portion of the main hollow section; connected to a portion of the main hollow section via a living hinge; removably connected to a portion of the main hollow section; and integrally formed with the main hollow section.

According to one non-limiting embodiment of the invention, the fixed part and the movable part each generally comprise one-half of an internal locking thread structured and arranged to engage with an external thread of the needle member.

According to one non-limiting embodiment of the invention, the member has one end which is fixed to the portion of the main hollow section.

According to one non-limiting embodiment of the invention, the member has one end which is removably connected to the portion of the main hollow section.

According to one non-limiting embodiment of the invention, the member has one end which is integrally formed with the main hollow section.

According to one non-limiting embodiment of the invention, the member has one end which is connected to the portion of the main hollow section via the living hinge.

According to one non-limiting embodiment of the invention, the safety cover is at least one of: pivotally mounted or connected to a portion of the needle member; movably mounted to a portion of the needle member; movable from a position not covering a proximal needle of the needle member to a position covering the proximal needle; and movable from an initial position to a locking position covering the proximal needle.

According to one non-limiting embodiment of the invention, the body is a one-piece member.

According to one non-limiting embodiment of the invention, the device further comprises guide projections arranged on the front end of the body.

According to one non-limiting embodiment of the invention, the front end comprises a through opening sized to receive an inner needle end of the needle member.

According to one non-limiting embodiment of the invention, the rear end comprises a flange.

According to one non-limiting embodiment of the invention, the device further comprises a locking mechanism that prevents the needle member from being reinstalled on the body.

According to one non-limiting embodiment of the invention, the device further comprises a mechanism for preventing re-use of the device.

According to one non-limiting embodiment of the invention, the device further comprises a mechanism for rendering the device single-use.

According to one non-limiting embodiment of the invention, there is provided a method of taking a fluid sample using any of the devices described above, wherein the method comprises installing the needle member, inserting a receptacle into the device, removing the receptacle from the device, and moving a safety cover to a needle covering position after use.

According to one non-limiting embodiment of the invention, there is provided a method of taking a fluid sample using any device described above, wherein the method comprises inserting a receptacle into the body, removing the receptacle from the body, and moving a safety cover to a needle covering position.

According to one non-limiting embodiment of the invention, there is provided a method of taking a fluid sample using any device described above, wherein the method comprises inserting a receptacle into the main hollow section, removing the receptacle, and preventing re-use of the device.

According to one non-limiting embodiment of the invention, there is provided a fluid collection device comprising a body having a front end, a back end, and a main hollow section arranged between the front and back ends and a needle hub securing section arranged on the front end and being structured and arranged to receive therein a needle member. The fluid collection/injection device is structured and arranged to utilize at least an operational mode, an operational mode, and a post-use mode. In the installation mode, the needle member is coupled to the body via the needle hub securing section. In the operational mode, fluid passes through the needle member and into a receptacle inserted into the main hollow section. In the post-use mode, a safety cover at least one of: prevents re-use of the fluid collection/injection device; prevents removal of the needle member from the fluid collection/injection device; prevents removal of the needle member from the needle hub securing section; activates release of the needle member from the body such that when the safety cover is in a position covering a needle of the needle member, the needle member can fall out of the needle hub securing section; activates release of the needle member from the body such that when the safety cover is in a position covering a needle of the needle member, the needle member is no longer securely retained to the needle hub securing section; releases a securing engagement between the needle member and the needle hub securing section; unlocks a locking connection between the needle member and the needle hub securing section; and moves a mechanism arranged in an area of the needle hub securing section which releases a connection between the needle member and the needle hub securing section.

According to one non-limiting embodiment of the invention, there is provided a needle assembly structured and arranged for use on a fluid collection device comprising a body having a front end, a back end, and a main hollow section arranged between the front and back ends, a needle hub securing section arranged on the front end and being structured and arranged to receive therein the needle assembly, the needle assembly being configured to operate in at least an operational mode, an operational mode, and a post-use mode. In the installation mode, the needle assembly being coupled to the body via the needle hub securing section. In the operational mode, fluid passes through a needle of the needle assembly into or out of a receptacle inserted into the main hollow section. In the post-use mode, a safety cover of the needle assembly at least one of prevents re-use of the fluid collection/injection device; prevents removal of the needle member from the fluid collection/injection device; prevents removal of the needle member from the needle hub securing section; activates release of the needle member from the body such that when the safety cover is in a position covering a needle of the needle member, the needle member can fall out of the needle hub securing section; activates release of the needle member from the body such that when the safety cover is in a position covering a needle of the needle member, the needle member is no longer securely retained to the needle hub securing section; releases a securing engagement between the needle member and the needle hub securing section; unlocks a locking connection between the needle member and the needle hub securing section; and moves a mechanism arranged in an area of the needle hub securing section which releases a connection between the needle member and the needle hub securing section.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 13 shows a side view of the needle member used on the needle assembly shown in FIG. 9 rotated 90 degrees;

FIG. 14 shows a side view of the needle member used on the needle assembly shown in FIG. 9;

FIG. 15 shows another non-limiting embodiment of a needle assembly according to the invention. The needle assembly includes a double-ended needle member, a removable cover, and a safety cover movable (or pivoted) from an initial position to a needle covering position. The removable cover and pivoting safety cover/shield is shown in cross-section;

FIG. 16 shows the needle assembly of FIG. 15 in the process of being installed on the body of FIGS. 3 and 4. After the user manipulates the body to allow the needle assembly to be installed therein, he/she may thereafter remove the removable cover;

FIG. 17 shows the needle assembly of FIG. 16 after removal of the removable cover. A torsion spring (not shown in FIGS. 15 and 16) is shown installed thereon;

FIGS. 18 and 19 show various views of the torsion spring shown in FIG. 17;

FIG. 20 shows another non-limiting embodiment of a needle assembly according to the invention. The needle assembly includes a double-ended needle member, a removable cover (not shown), and a safety cover or shield movable (or pivoted) from an initial position to covering position. In FIG. 20, the safety cover is shown locked in the covering position;

In FIG. 24, the user moves the safety cover to the locked covering position which causes the portion of the body retaining the needle to open and allows for removal of the needle assembly;

In FIG. 24, the user must discard the entire device because the safety cover is locked via a lock retainer and prevents the user from opening the portion of the body retaining the needle assembly. The device is thereby rendered single-use;

FIG. 27 shows how the safety cover does not prevent or obstruct removal of the needle assembly from the body in FIG. 27;

FIGS. 32-24 show various enlarged views of another non-limiting embodiment of the device in accordance with the invention. This embodiment utilizes another embodiment of a needle assembly, which is shown already installed on the body in FIG. 32. In this embodiment, an activatable locking ring is utilized to prevent removal of the needle assembly from the body only when the safety cover is in the covering position. Once the needle assembly is installed, it can be removed by unthreading it from the body. On the other hand, after use of the device, the safety cover can be moved to the covering position shown in FIG. 34, and, when locked therein, prevents the needle assembly from being removed. At this point, the entire device can, should and/or must be discarded.

DETAILED DESCRIPTION OF THE INVENTION

Figure 1:
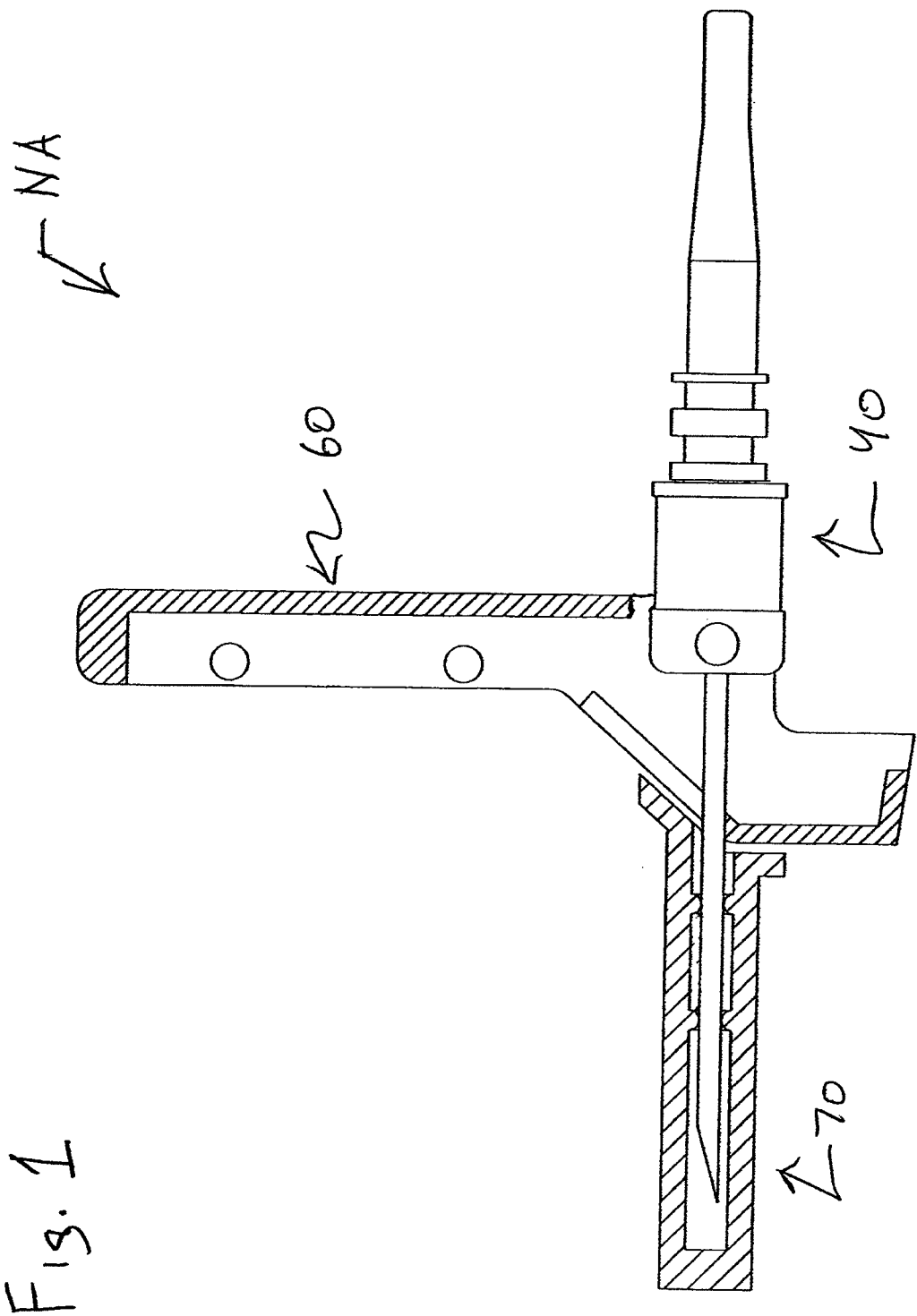
FIG. 1 shows a side view of one non-limiting embodiment of a needle assembly according to the invention. The needle assembly includes a double-ended needle member, a removable cover, and a safety cover movable (or pivoted) from an initial position to a needle covering position. The removable cover and pivoting safety cover/shield is shown in cross-section.

FIGS. 1-14 show one non-limiting embodiment of the invention. FIG. 1 shows one non-limiting embodiment of a needle assembly NA according to the invention. The needle assembly NA includes a double-ended needle member 40, a removable cover 70, and a safety cover or shield 60 movable (or pivoted) from an initial position (see FIG. 5) to a needle covering position (see FIG. 6). The removable cover 70 will typically be installed when the needle assembly NA is packaged and remains installed until the needle assembly NA is installed on the body 10.

Figure 2:
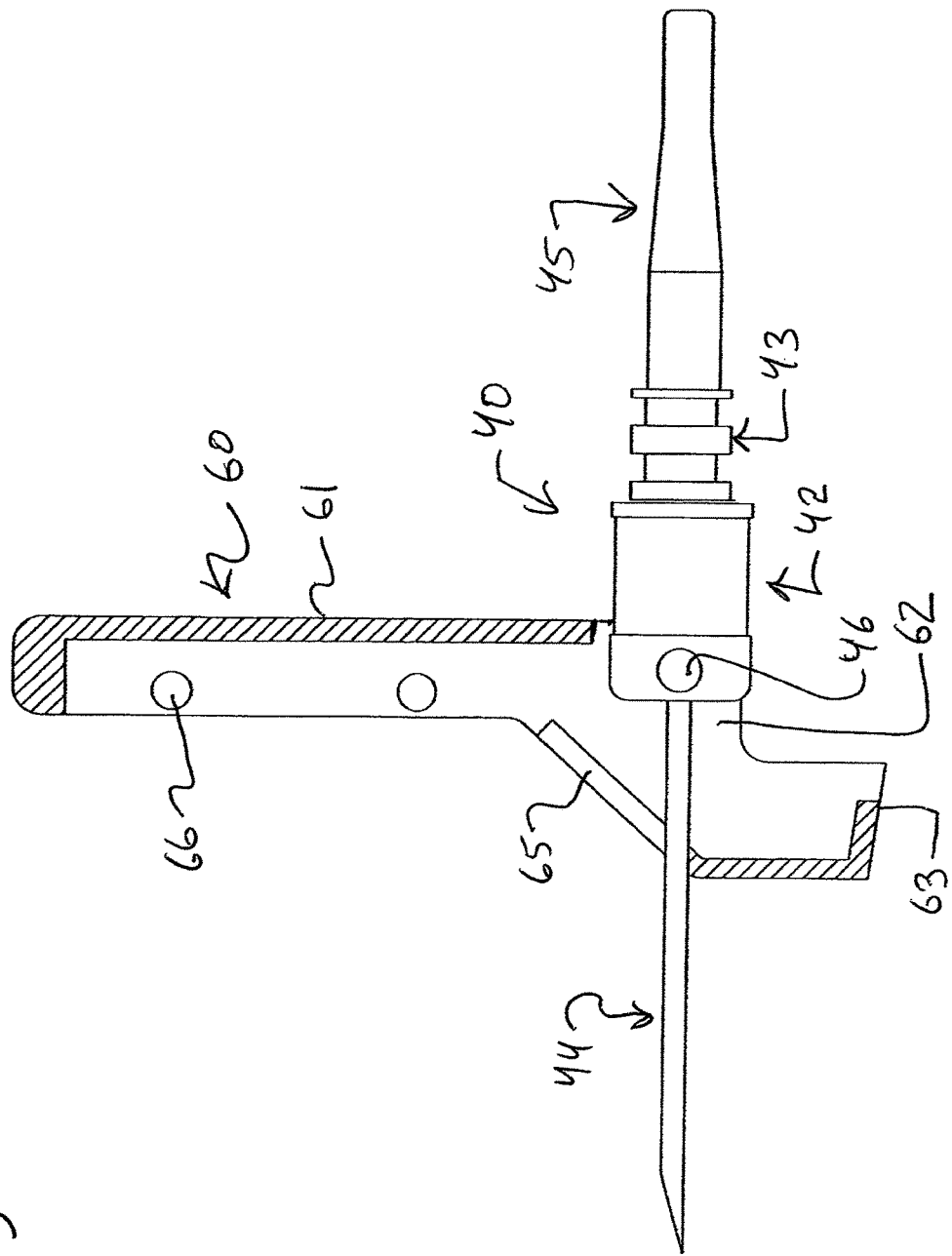
FIG. 2 shows the needle assembly of FIG. 1 with the removable cover removed.
Figure 3:
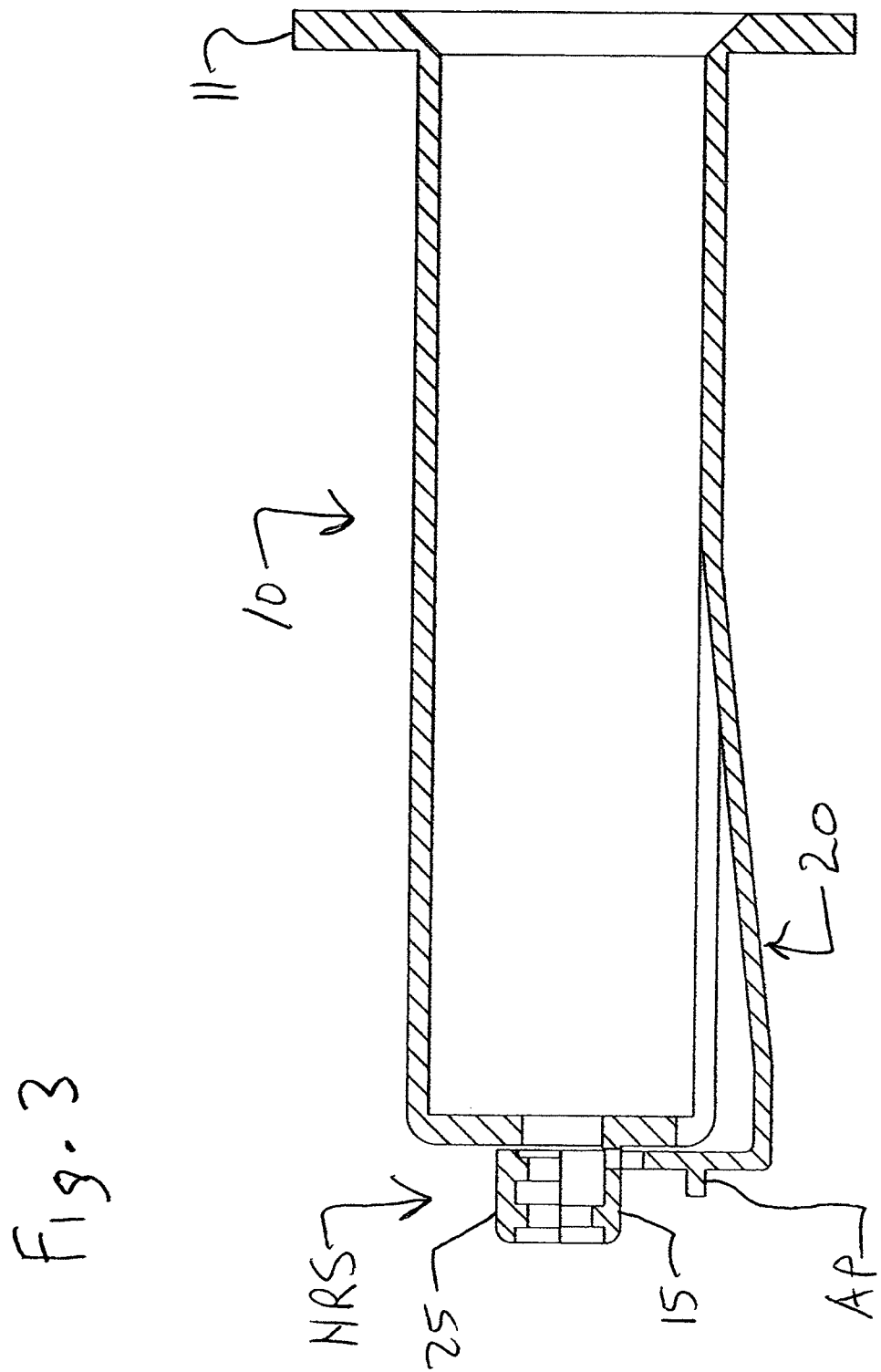
FIG. 3 shows a side view of one non-limiting embodiment of a body for a fluid collection device in accordance with the invention. The body is shown in cross-section and in an initial, original and/or normal position.

With reference to FIGS. 2, 13 and 14, it can be seen that the needle member 40 of the needle assembly NA includes a first hollow needle (not shown) but arranged within flexible puncturable cover 45 as is the case with conventional fluid sampling needle members, a main body 42, an external thread 43 for threading into the internal thread of the body 10, a second hollow or injection needle 44, and two oppositely arranged mounting projections 46 to which the needle cover 60 can be pivotally mounted. In embodiments, the needle member 40 can be of any conventional type provided it can be modified to include a mechanism for movably mounting the cover 60. As is the case with some known double-ended needle assemblies, the body 42 can include an elastically compressible section which is compressed when installed on the device (see accordion configuration of body in FIG. 5). Furthermore, although the needle member 40 utilizes projections 46 to mount the cover 60, the invention contemplates utilizing openings on the body 42 instead of projections 46 and projections on the cover 60 instead of openings 64 (see FIG. 10).

With reference to FIGS. 2 and 10-12, it can be seen that the needle cover or shield 60 of the needle assembly NA includes an elongated needle covering portion 61 defining an internal space for retaining therein the needle 44, main body sidewalls 62, an engaging shoulder 63, two oppositely arranged mounting openings 64 receiving therein one of the projections 46 and allowing the cover 60 to be pivotally mounted to the needle member 40, needle receiving slot 65 sized to receive therein the needle 44, and plural oppositely arranged engaging and locking projections 66. The projections 66 can deflect somewhat to allow the needle 44 to pass thereby and have rounded ends to facilitate the same. Of course, the free ends of the projections 66 can have any shape (such as tapered ends) so as to allow the needle 44 to pass thereby while also preventing the needle 44 from then passing by in the opposite direction—once in the locked position, the cover 60 cannot become unlocked based on the configuration of the projections 66. In embodiments, a spacing (see FIG. 12) between the free ends of the opposite projections 66 is sized to be smaller than the diameter of the needle 44 so that when the cover 60 is moved to the position shown in FIG. 6, the engagement is such that prevent the cover 60 from being pivoted back to the initial position. In embodiments, the cover 60 is a one-piece member. However, the invention contemplates utilizing a multi-piece member.

Figure 4:
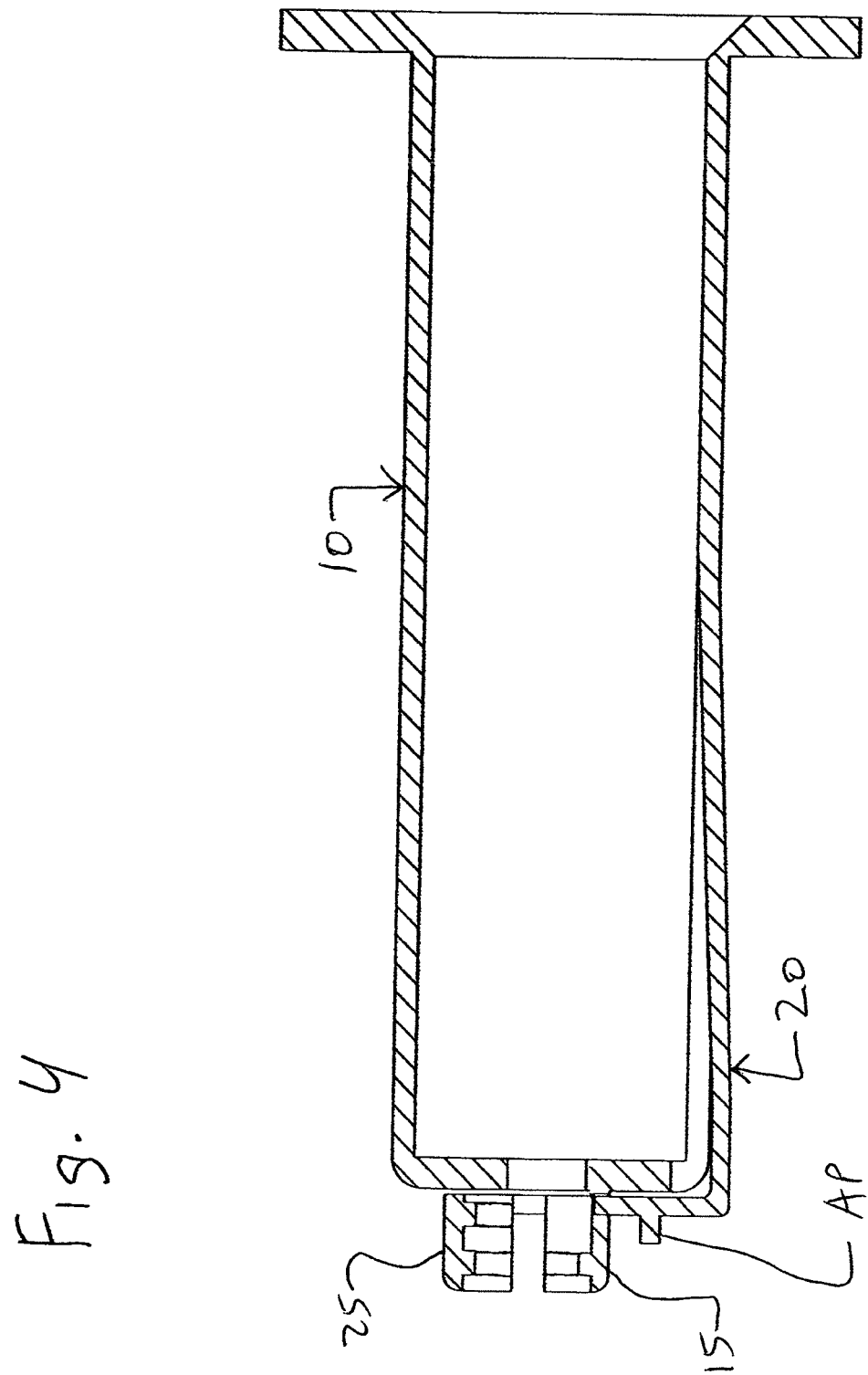
FIG. 4 shows the body of FIG. 3 in an activated, open and/or needle releasing position.

With reference to FIGS. 3-8, it can be seen that the body 10 includes an elongated main opening sized to contain therein a proximal end a container or vial which will receive the fluid sample as with conventional devices, a flange 11 also used on conventional devices, and a needle receiving standard interface NRS used on conventional devices. However, unlike conventional devices, the body 10 and interface NRS utilizes a deflectable element 20 having an activatable portion AP and a movable jaw or retaining portion 25. A fixed jaw or retaining portion 15 is arranged on the body 10. As can be seen in FIG. 4, when the user moves the deflectable portion 21, the movable jaw 25 coupled thereto moves to the open position so that needle assembly NA can disengage from the interface NRS and fall out of the body 10.

Figure 5:
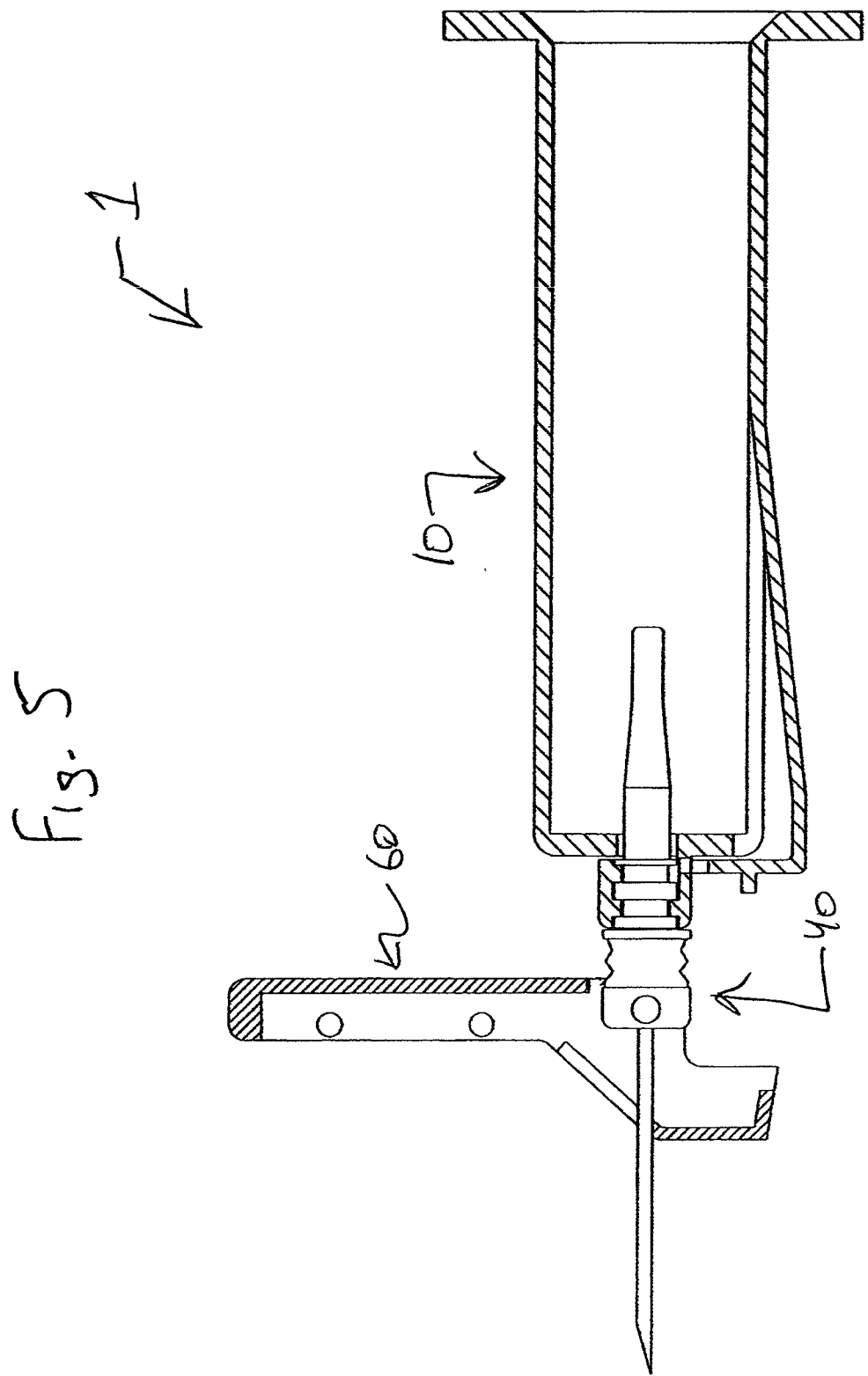
FIG. 5 shows the needle assembly of FIG. 2 installed on the body of FIG. 3. Normally, the needle assembly of FIG. 1 is threaded or slid into the body when in the open position shown in FIG. 4 (this can preferably occur in a factory setting). The body is then allowed to assume the normal position (and packaged in this state with the removable cover installed). At the time of use, a user removes the device from its packaging, and then removes the removable cover. The device is then ready for use and is shown in a use position/configuration.

FIG. 5 shows the needle assembly NA installed on the body 10 of the fluid sampling device 1. In embodiments, the needle assembly NA is threaded (or optionally slid) into the body 10 when placed by the user in the open position shown in FIG. 4. In embodiments, this can occur in a factory setting so that the device of FIG. 5 is packaged as is with the removable cover 70 installed thereon. On the other hand, if the needle assembly NA is installed by a user at the time of use, after installation the body 10 can be allowed to assume the normal or use position shown in FIG. 5. At the time of use, a user ideally removes the removable cover 70 only immediately before use for fluid sampling.

Figure 6:
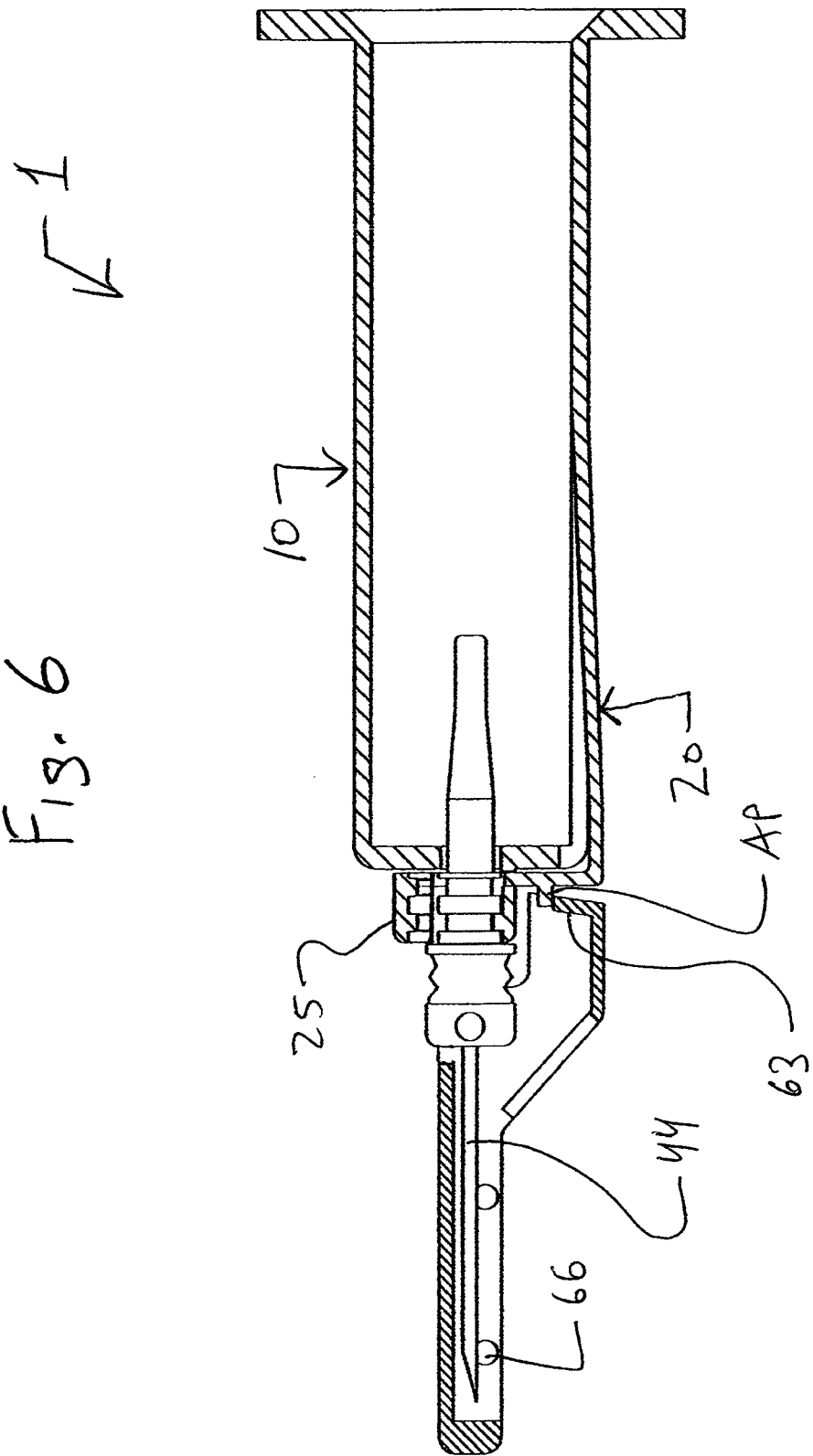
FIG. 6 shows the device of FIG. 5 after the safety cover or shield is moved and locks in the covering position. The device shown is in a post-use position. Movement of the safety cover to the locked covering position has automatically caused the portion of the body retaining the needle assembly to disengage there from. The needle assembly can now be removed safely from the body by simply pulling it off or allowing it to drop out and into a sharps container.
Figure 7:
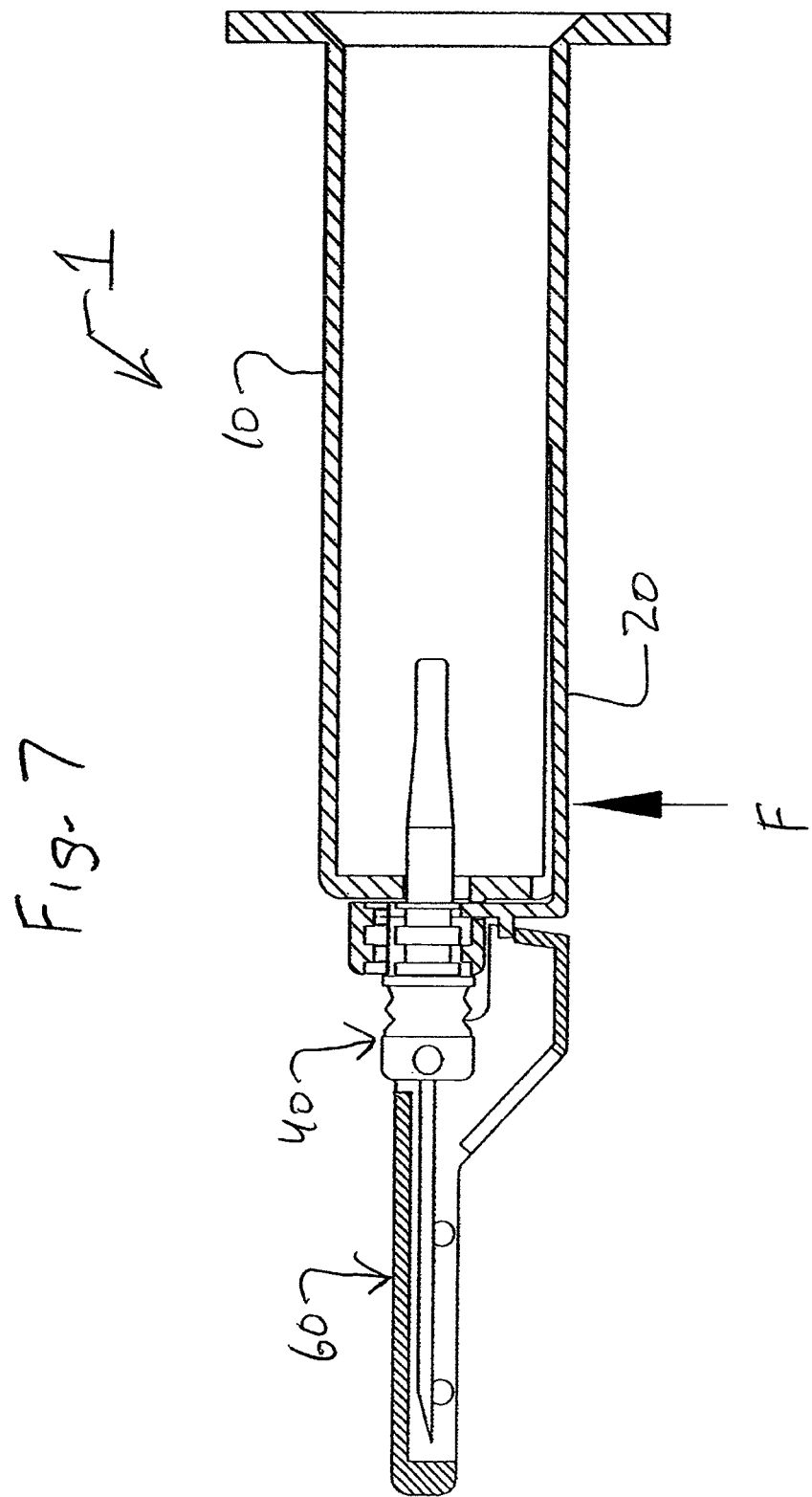
FIG. 7 shows the device of FIG. 6 with the user optionally applying a force to maintain open the portion of the body that retains the needle assembly.
Figure 8:
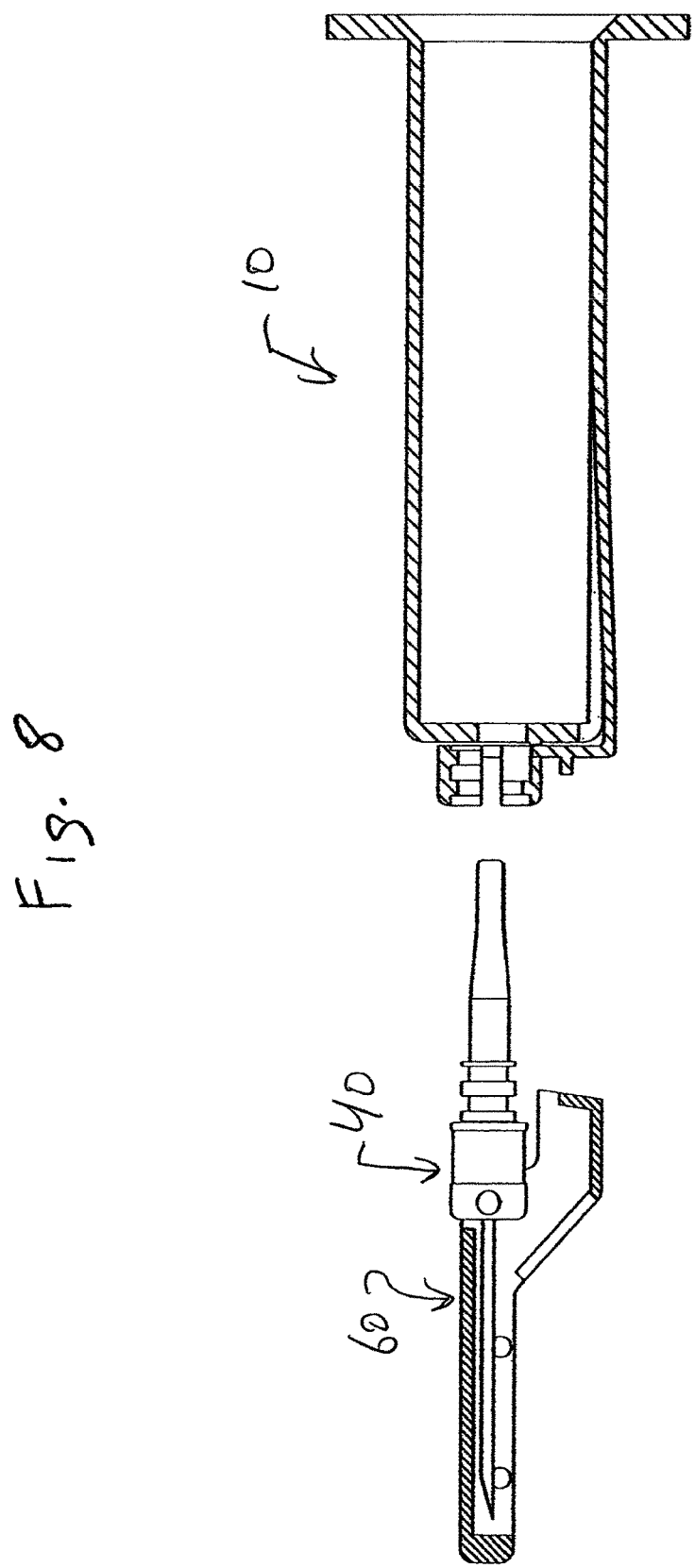
FIG. 8 shows the device of FIG. 6 after the needle assembly is removed from the body. The needle assembly can now be safely discarded. The body can also discarded or possibly re-used. Once the user stops gripping the body, it will return to the normal, position.
Figure 9:
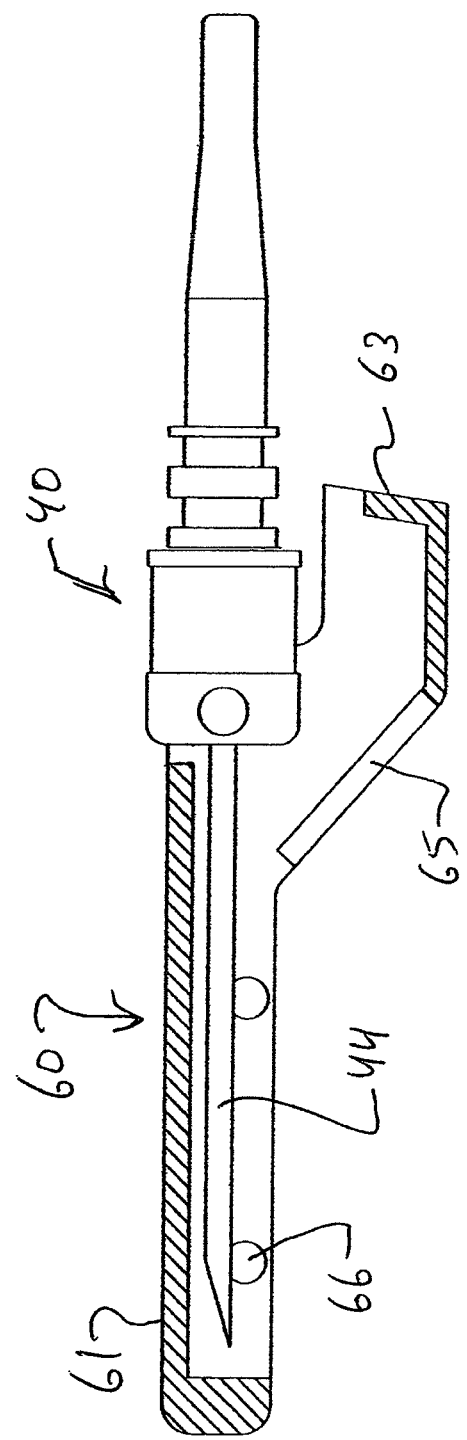
FIG. 9 shows an enlarged view of the needle assembly shown in FIG. 8.
Figure 10:
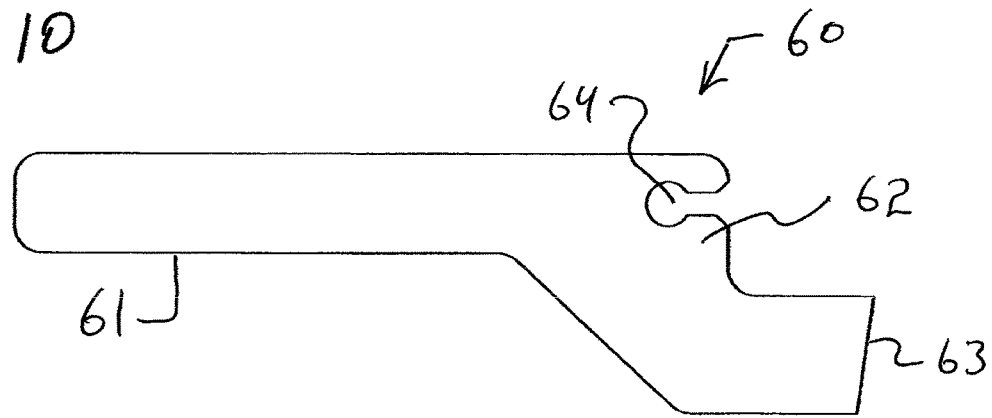
FIG. 10 shows a side view of the safety cover or shield used on the needle assembly shown in FIG. 9.
Figure 11:
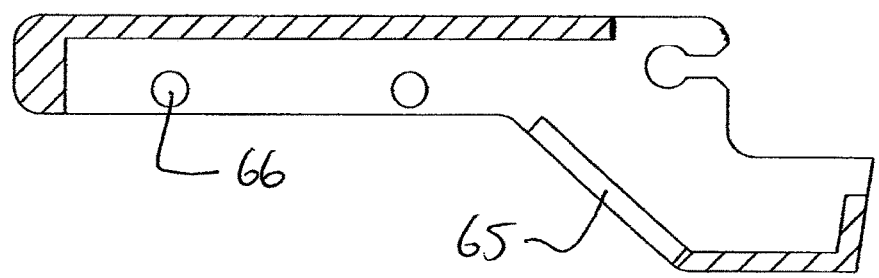
FIG. 11 shows a side cross-section view of FIG. 10.
Figure 12:
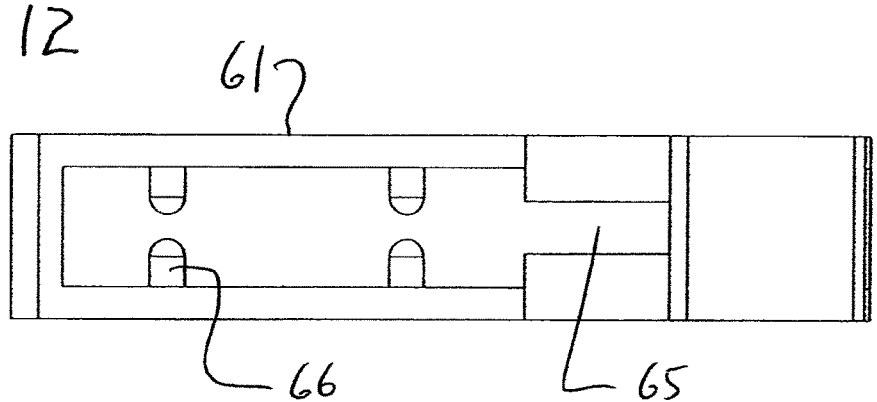
FIG. 12 shows a bottom view of FIG. 10.
Figure 21:
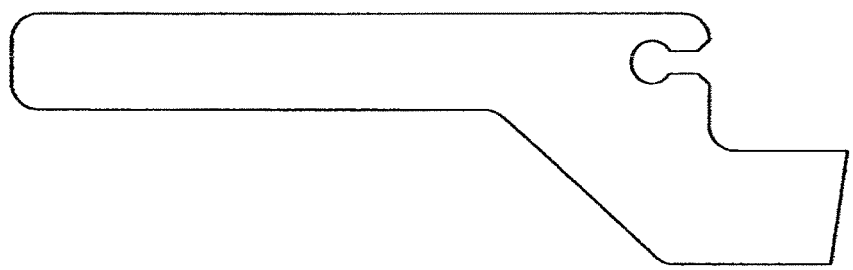
FIGS. 21-23 show side, cross-section and bottom views of the safety cover or shield used on the needle assembly shown in FIG. 20.
Figure 22:
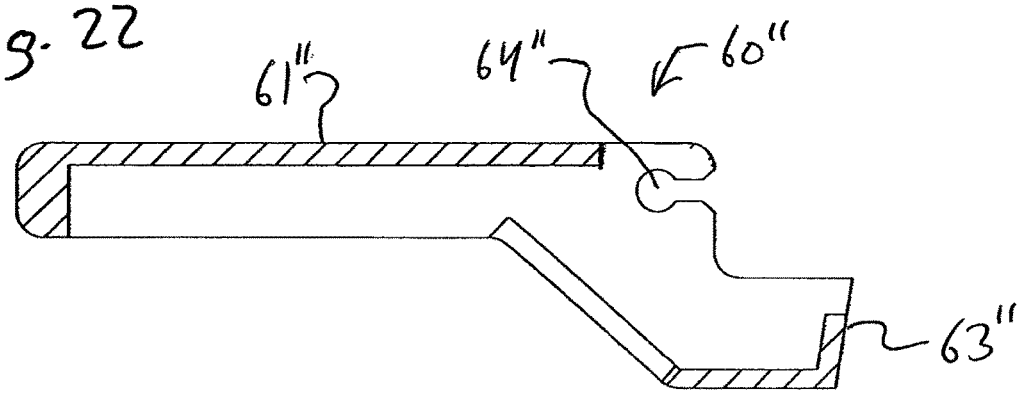
Figure 23:
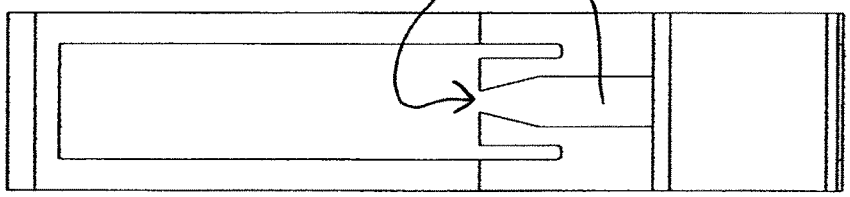

FIG. 6 shows the device 1 of FIG. 5 used and after the safety cover or shield 60 is moved and locks in the covering position. The device 1 is thus shown in a post-use position. To place the device 1 in this position, the user simply grips the shield 60 and rotates or pivots it from the position shown in FIG. 5 to that of FIG. 6. Movement of the safety cover 60 to the position shown in FIG. 6 causes it to become locked in covering position owing to the locking engagement between the projections 66 and the needle 44. This movement also simultaneously and/or automatically causes the portion 25 of the body 10 retaining the needle assembly NA to disengage there from. This is as a result of the shoulder or wall 63 contacting and causing movement of the activating projection AP. This can also be facilitated or assisted by the user pressing on the element 20 toward the body 10 as illustrated by arrow F in FIG. 7. The needle assembly NA can now be removed safely from the body 10 by simply pulling it off or allowing it to drop out (under the force of gravity) of the body 10 as illustrated in FIG. 8. Preferably, at least the needle assembly NA in the safely locked configuration shown in FIG. 9 is allowed to fall into a sharps container.

As should be apparent from FIGS. 1, 2 and 9-12, the configuration of the safety cover or shield 60 is such that the slot 65 allows the needle 44 to move therein (or vice versa) the with the closed end of the slot 65 contacting (and serving as a stop) the needle 44 in the position shown in FIG. 2.

FIGS. 15-19 show another non-limiting embodiment of the invention. FIG. 15 shows another non-limiting embodiment of a needle assembly NA' according to the invention. The needle assembly NA' includes a double-ended needle member 40', a removable cover 70', and a safety cover or shield 60' movable (or pivoted) from an initial position (see FIG. 15) to a use position (see FIG. 17) to a needle covering position (not shown but similar to FIG. 20). The removable cover 70' will typically be installed when the needle assembly NA' is packaged and remains installed until the needle assembly NA' is installed on the body 10.

As can be seen in FIG. 16, installation can occur when the needle assembly NA' is threaded or slid into the body 10. This is facilitated when the use places the body 10 in the open position. At this point, the use can remove the removable cover 70'. When this happens, the safety cover or shield 60' will automatically move (or pivot) from an initial position (see FIG. 15) to the use position (see FIG. 17) via one or more torsion springs 80 (see FIGS. 17-19). In embodiments, a single spring 80 is mounted to one of the projections 46' and is arranged to bias the shield 60' towards the use position as shown in FIG. 17. Although this embodiment can preferably utilize a cover similar to that of FIGS. 20-23 (described in detail below), the invention contemplates the user moving the shield 60' against the biasing force of the spring 80 back to the position shown in FIG. 15 and, while retained therein, the cover 70' being reinstalled. In other embodiments, the spring 80 is reconfigured so that it biases the cover 60' towards the closed or covering portion shown in FIG. 15 and can be moved to the open or use position shown in FIG. 17 only against the biasing force of the spring.

FIGS. 20-23 show another non-limiting embodiment of the invention. FIG. 20 shows another non-limiting embodiment of a needle assembly NA" according to the invention. The needle assembly NA" includes a double-ended needle member 40", an optional removable cover (not shown, but similar to cover 70') and a safety cover or shield 60" movable (or pivoted) from an initial position (not shown but similar to that of see FIG. 1) to a use position (not shown but similar to FIG. 2) to a needle covering position (see FIG. 20). After installation of the needle assembly NA" and removable of the removable cover, the device is used for fluid sampling. Thereafter, the user moves the shield 60" to the locked and closed position shown in FIG. 20. Unlike the embodiment of FIG. 1, however, non-releasable locking occurs via deflectable locking members 67" (see FIG. 23).

Figure 24:
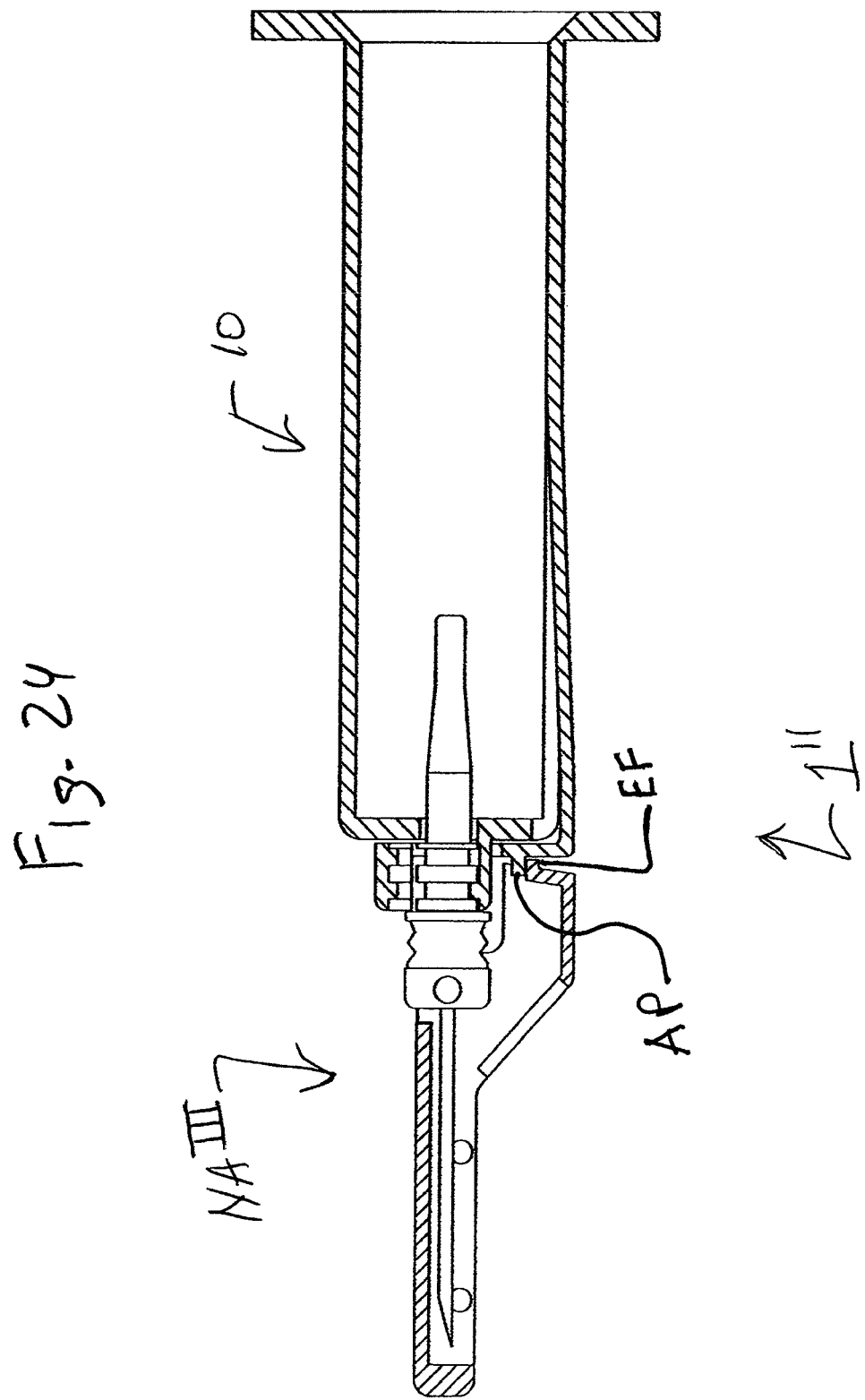
FIG. 24 shows a non-limiting embodiment of the device utilizing another embodiment of a needle assembly having an engaging flange, which is shown being removed from the body of FIGS. 3 and 4 after use.

FIG. 24 shows another non-limiting embodiment of the device 1". In this embodiment, the needle assembly $NA^{III}$ is similar to that of FIG. 2, but additionally includes an engaging flange EF arranged on the safety cover or shield. The engaging flange EF is such when it is moved (or pivoted) from a use position to a needle covering position (as is apparent from FIG. 24) the engaging flange EF contacts or engages with the activatable projection AP and causes the needle retaining interface of the device body 10 to open so that the needle assembly $NA^{III}$ can fall out or otherwise be easily removed.

Figure 25:
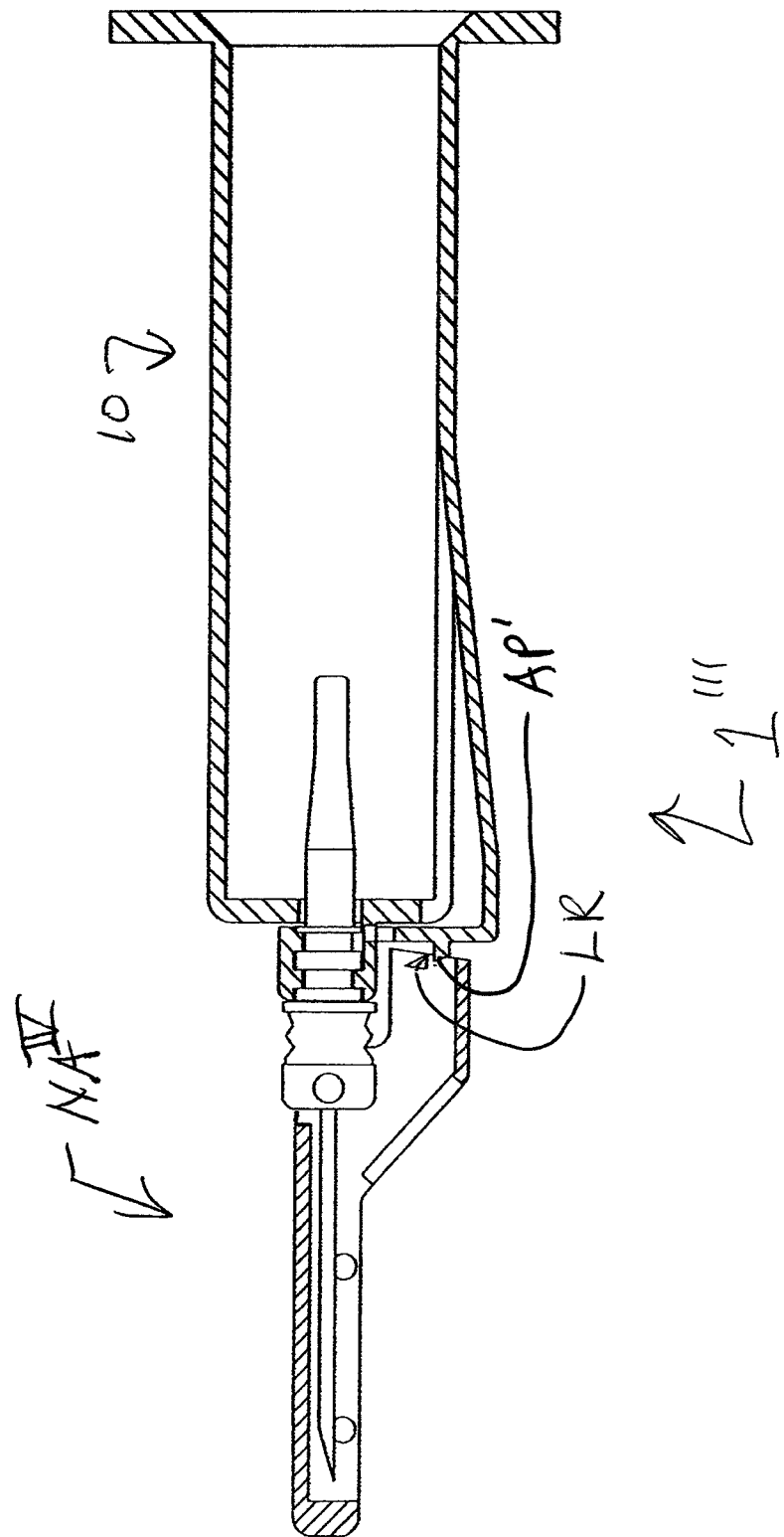
FIG. 25 shows a non-limiting embodiment of the device utilizing another embodiment of a needle assembly, which is shown preventing removal of the needle assembly from the body.

FIG. 25 shows another non-limiting embodiment of the device 1'''. In this embodiment, the needle assembly $NA^{IV}$ is similar to that of FIG. 2, but additionally includes a lock retainer LR arranged on the safety cover or shield. The lock retainer LR is such when it is moved (or pivoted) from a use position to a needle covering position (as is apparent from FIG. 25), the lock retainer LR contacts or engages with the activatable projection AP' and causes the needle retaining interface of the device body 10 to open so that the needle assembly $NA^{IV}$ can fall out or otherwise be easily removed. Furthermore, the tapered configuration of the lock retainer LR and the activatable projection AP' is such that once the needle shield is positioned (which is allowed to happen by the tapered engaging surfaces) in the covering position shown in FIG. 25, the needle shield is prevented from moving back to the use position by the engagement between the lock retainer LR (and the recess disposed behind the same) and the activatable projection AP'. Additionally, the tapered configuration of the lock retainer LR and the activatable projection AP' is such that as the needle shield is positioned in the covering, engagement between the tapered surfaces followed by release of the same causes a clicking sound—thereby providing an audible signal to the user that the device is locked. In the locked position shown in FIG. 25, the device 1''' is rendered unusable (making the device single-use) and can then be safely disposed of with both needles of the needle assembly $NA^{IV}$ protected, i.e., the distal needle is safely arranged within the device body 10 and the proximal or injection needle is covered by the needle shield.

Figure 26:
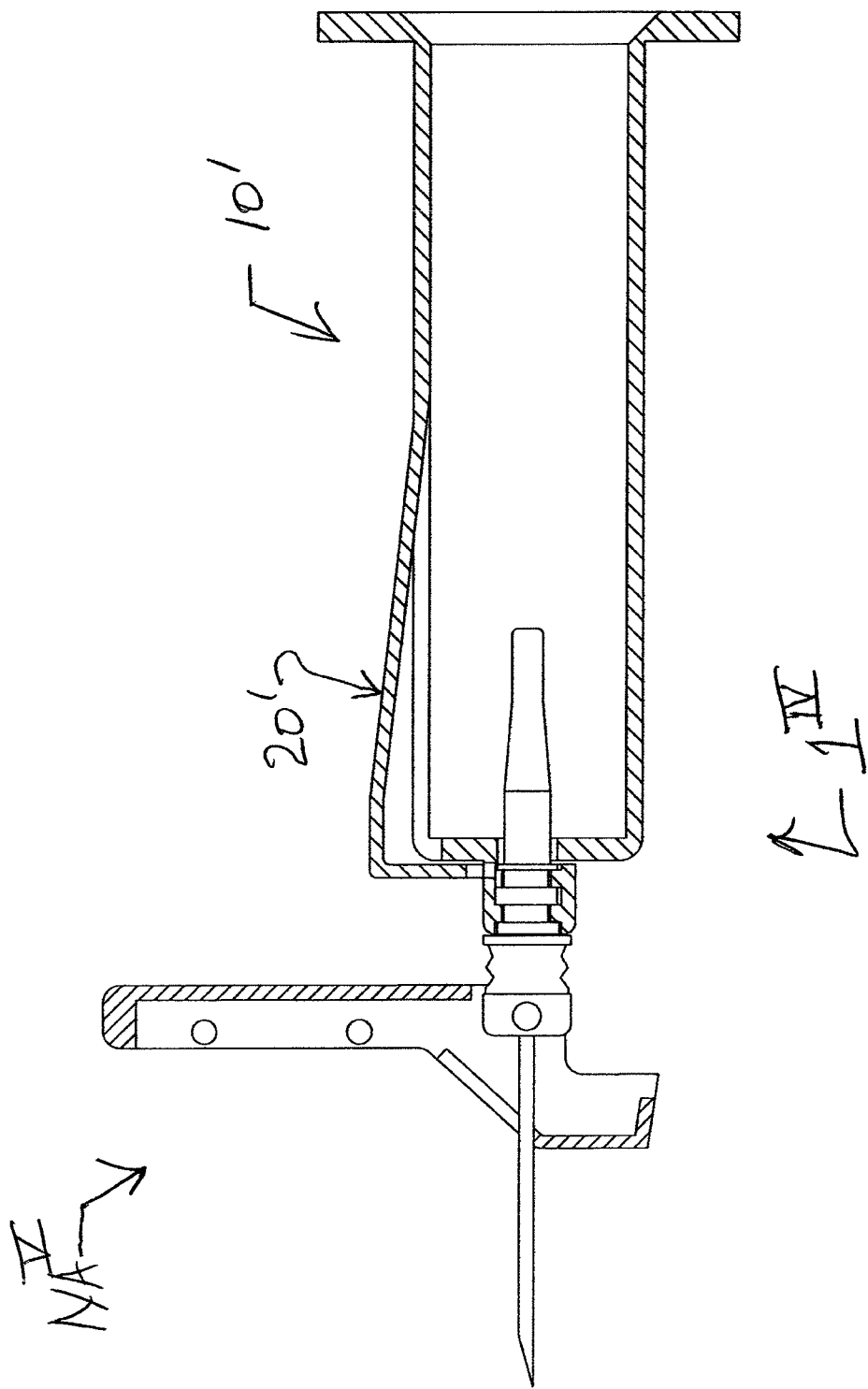
FIGS. 26 and 27 show side views of another non-limiting embodiment of the device. The needle assembly in this embodiment can be installed at the time of use and is shown already installed on the body in FIG. 26 and after the removable cover is removed.
Figure 27:
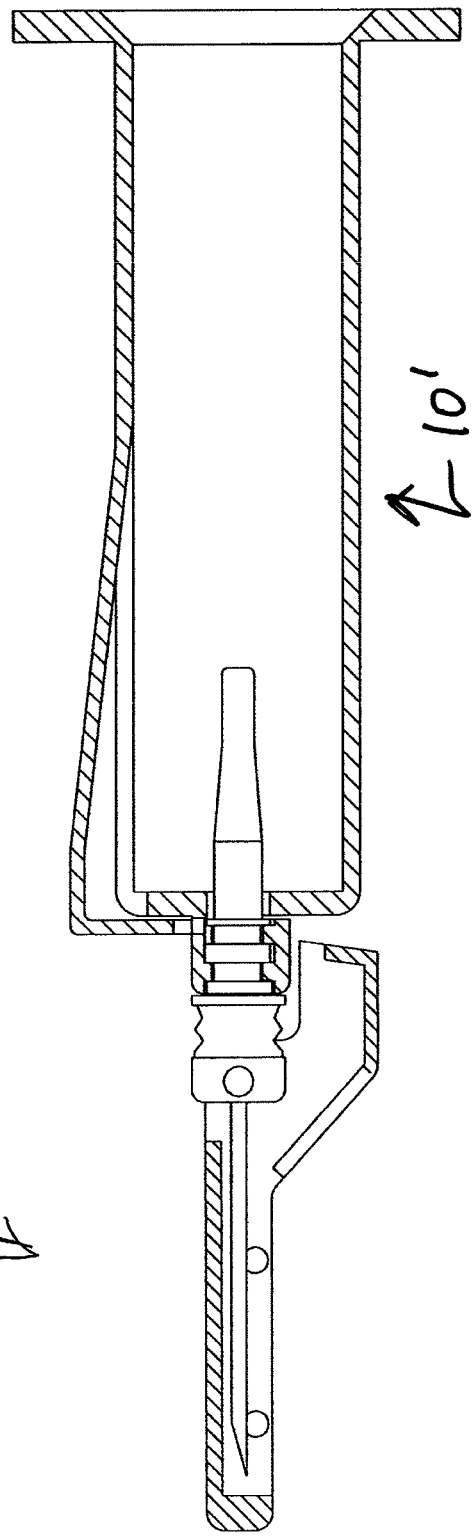

FIGS. 26-27 show another non-limiting embodiment of the device $1^{IV}$. In this embodiment, the needle assembly $NA^{V}$ is similar to that of FIG. 2, but is utilized with a different device body 10'. The device body 10' is different in that it lacks an activatable projection AP. As such, no part of the needle shield contacts or engages with an activatable projection AP and/or any part of the device body 10' when the needle assembly $NA^{V}$ is placed in any of its positions, i.e., the use and covering position. For example, in the use position shown in FIG. 26, the needle assembly $NA^{V}$ can be used while being retained on the body 10'. However, it can also be removed by moving member 20' toward the body 10'. Although this is not recommended, this embodiment allows for such to happen at the user's discretion. In the post-use position shown in FIG. 27, the needle assembly $NA^{V}$ can be rendered un-usable while being retained on the body 10'. Moreover, it can also be removed by moving member 20' toward the body 10'.

Although this is not recommended, this embodiment allows for such to happen at the user's discretion—in case the user wishes to reuse the body 10', i.e., by installing another, a new and/or un-used needle assembly $NA^{V}$.

Figure 28:
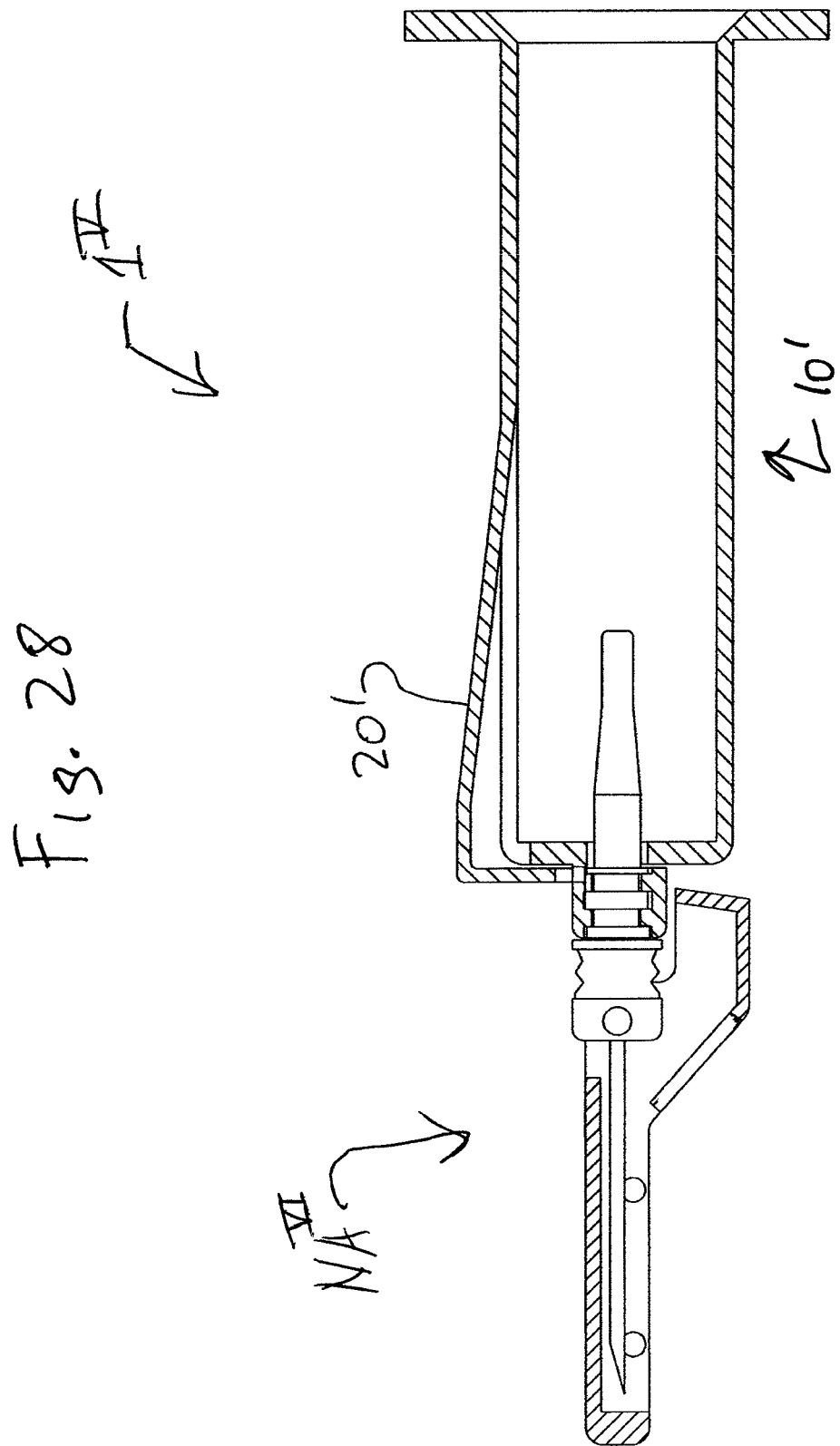
FIG. 28 shows another non-limiting embodiment of the device utilizing another embodiment of a needle assembly, which is shown already installed on the body with the safety cover locked in the covering position and preventing removal of the needle assembly from the body.

FIG. 28 show another non-limiting embodiment of the device $1^{V}$. In this embodiment, the needle assembly $NA^{VI}$ is similar to that of FIG. 2, but additionally utilizes the needle shield locking arrangement 65"/67" shown in FIG. 23 so as to provide a secondary and/or back-up and/or redundant and/or dual locking system. The device body 10' is otherwise similar to that of FIGS. 26-27 and can be used in a similar manner.

Figure 29:
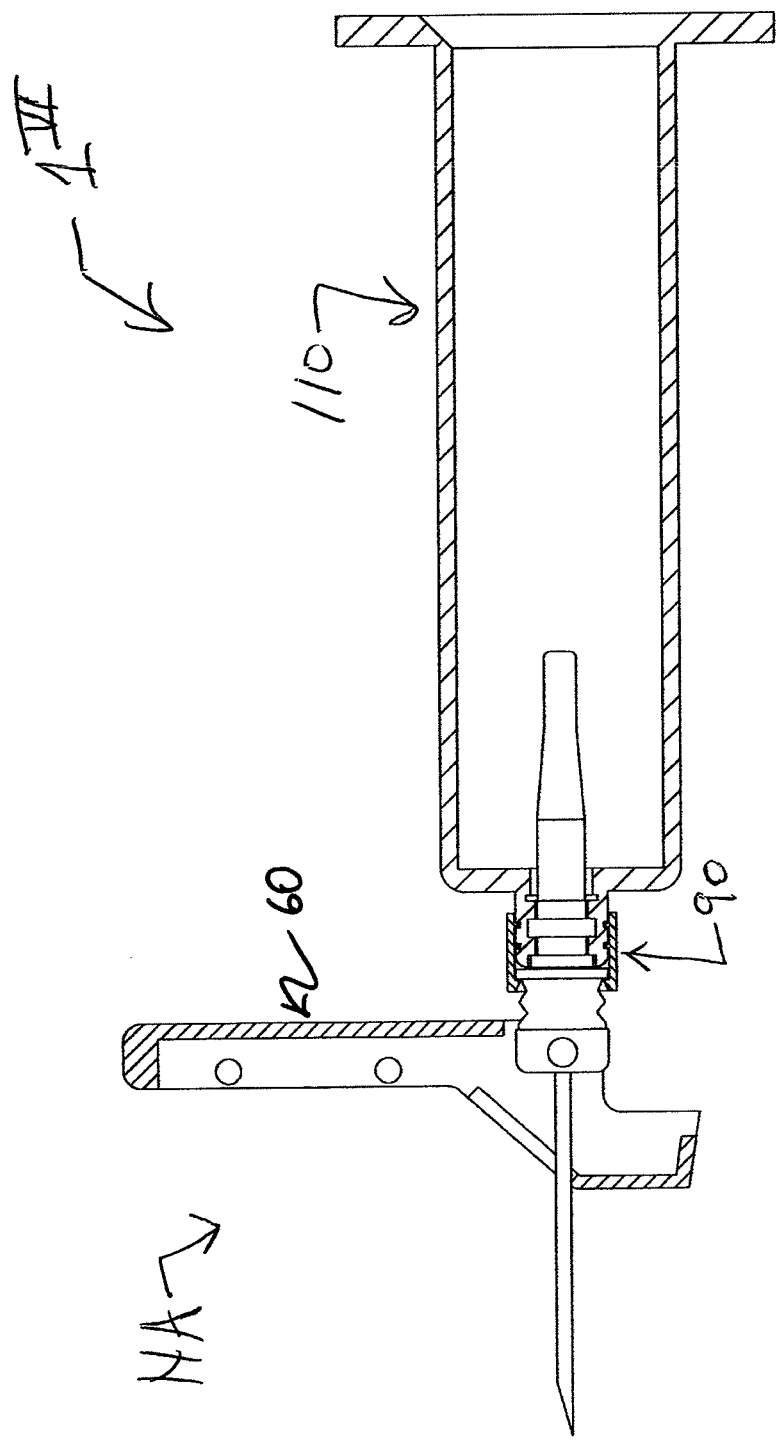
FIG. 29 shows another non-limiting embodiment of the device in accordance with the invention. In this embodiment, the needle assembly of FIG. 1 is shown already installed on the body. The body utilizes a locking ring to prevent removal of the needle assembly from the body after it is threaded therein and regardless of the position of the safety cover. Once the needle assembly is installed, it cannot be removed. After use, the safety cover can be moved to the covering position and the entire device can be discarded.
Figure 30:
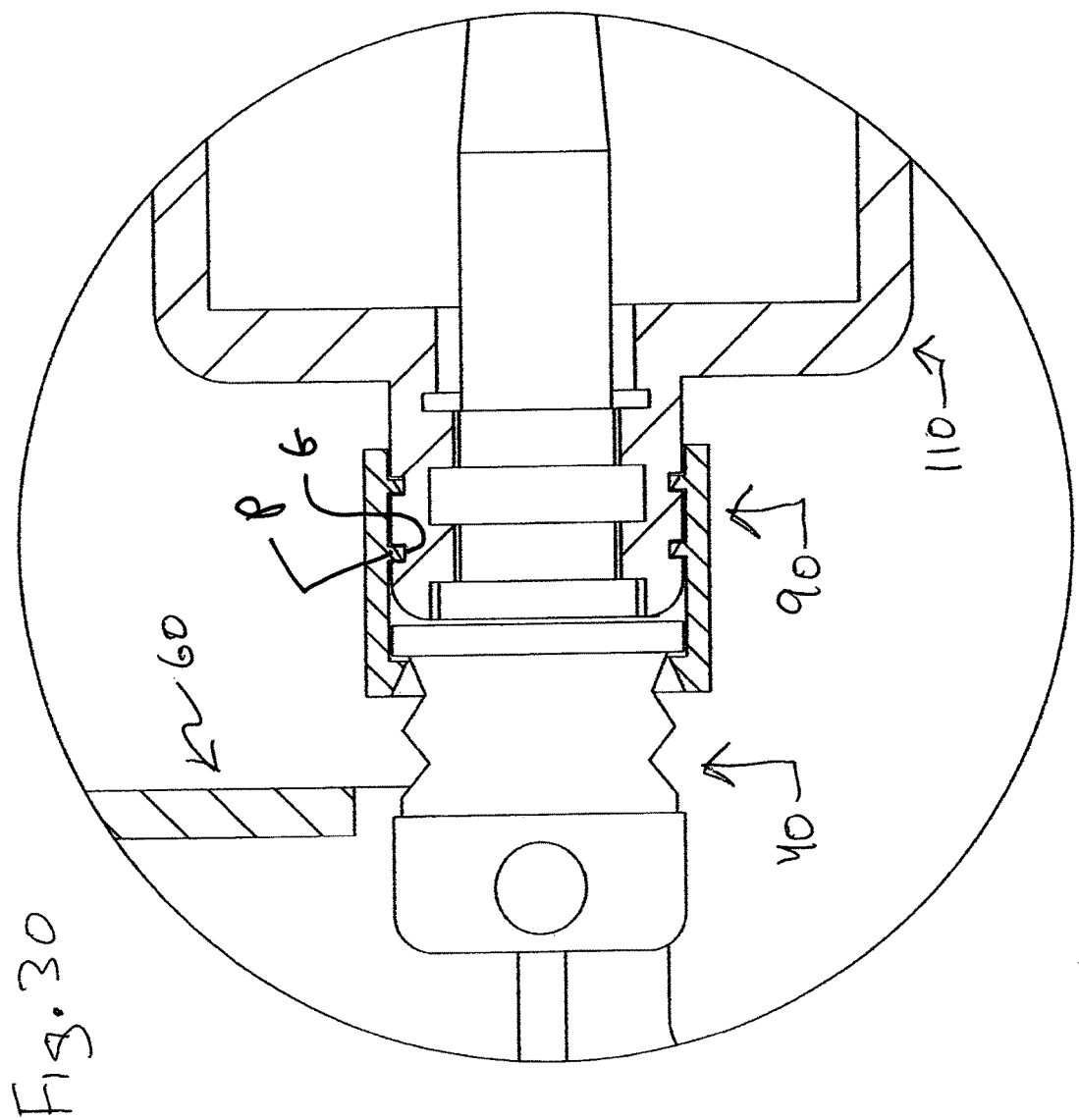
FIG. 30 shows an enlarged view of a portion of FIG. 29.
Figure 31:
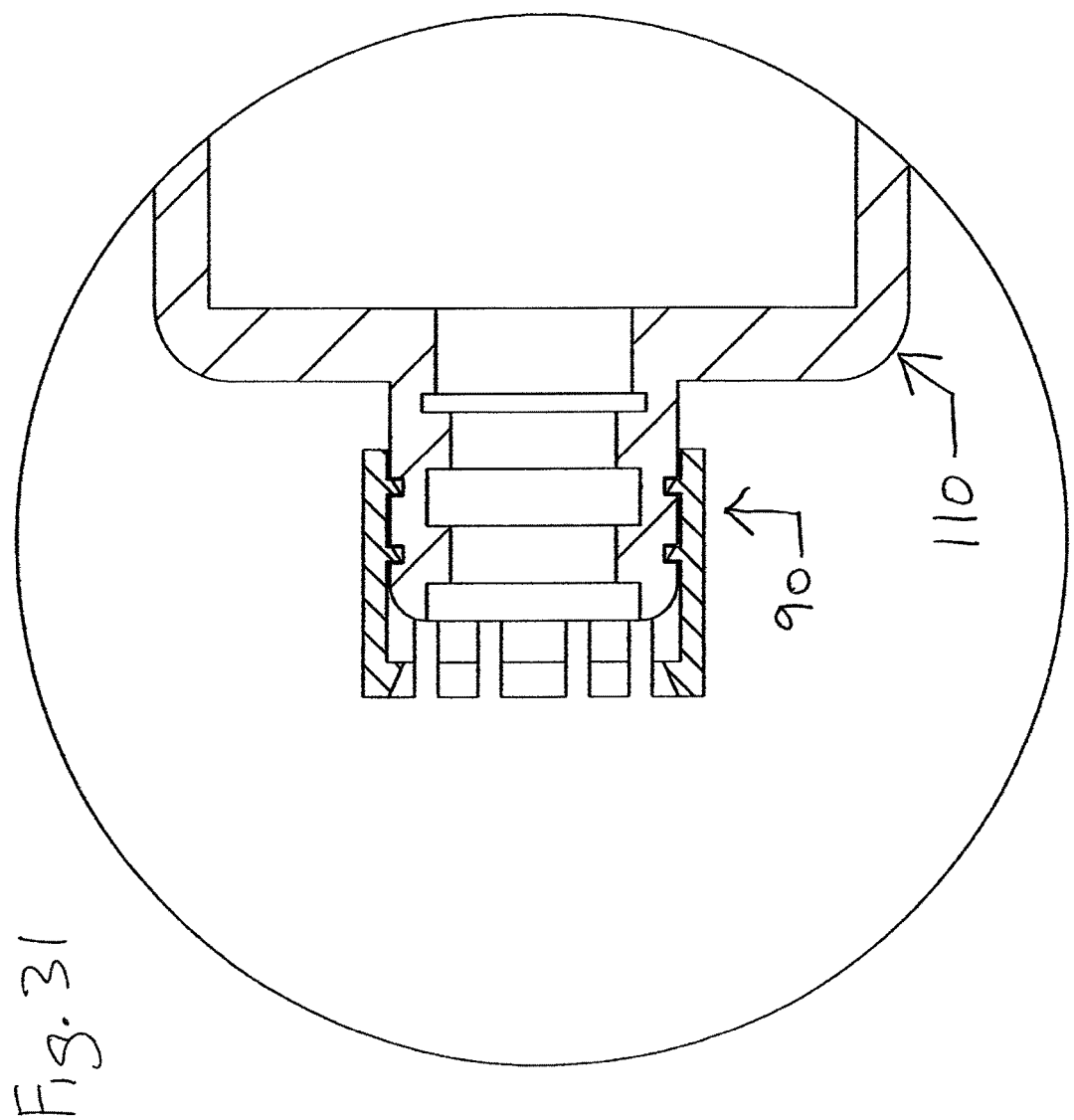
FIG. 31 shows an enlarged view of a portion of FIG. 29 prior to installation of the needle assembly.

FIGS. 29-31 show another non-limiting embodiment of the device $1^{VI}$ in accordance with the invention. In this embodiment, the needle assembly NA of FIG. 1 is shown already installed on a device body 110. The body 110 utilizes a locking ring 90 on the connecting interface to prevent removal of the needle assembly NA from the body 110 after it is threaded therein. As such, no deflectable member (i.e., member 20 in FIG. 3) need be utilized. The ring 90 (or more specifically the tapered configuration of the front-side deflectable fingers of the ring 90 (see FIG. 31) engaging with a flange or shoulder of the member 40) is configured such that one can thread on (or otherwise install) the needle assembly NA, but, once fully threaded therein or installed, prevents its removal regardless of the position of the safety cover or needle shield 60. As can be seen in FIG. 30, full insertion causes elastic compression (illustrated by an accordion or corrugated shape) of the body of the needle member 40. Once the needle assembly NA is installed, it cannot be removed even after use. After use, the safety cover 60 is moved to the covering position and the entire device $1^{VI}$ can (or more properly, must) be discarded as a connected unit. In embodiments, the ring 90 is made out of a spring type material such as, e.g., spring steel, and be a sprit ring so as to facilitate seating of the circumferential projections P with the circumferential grooves G (see FIG. 30).

Figure 32:
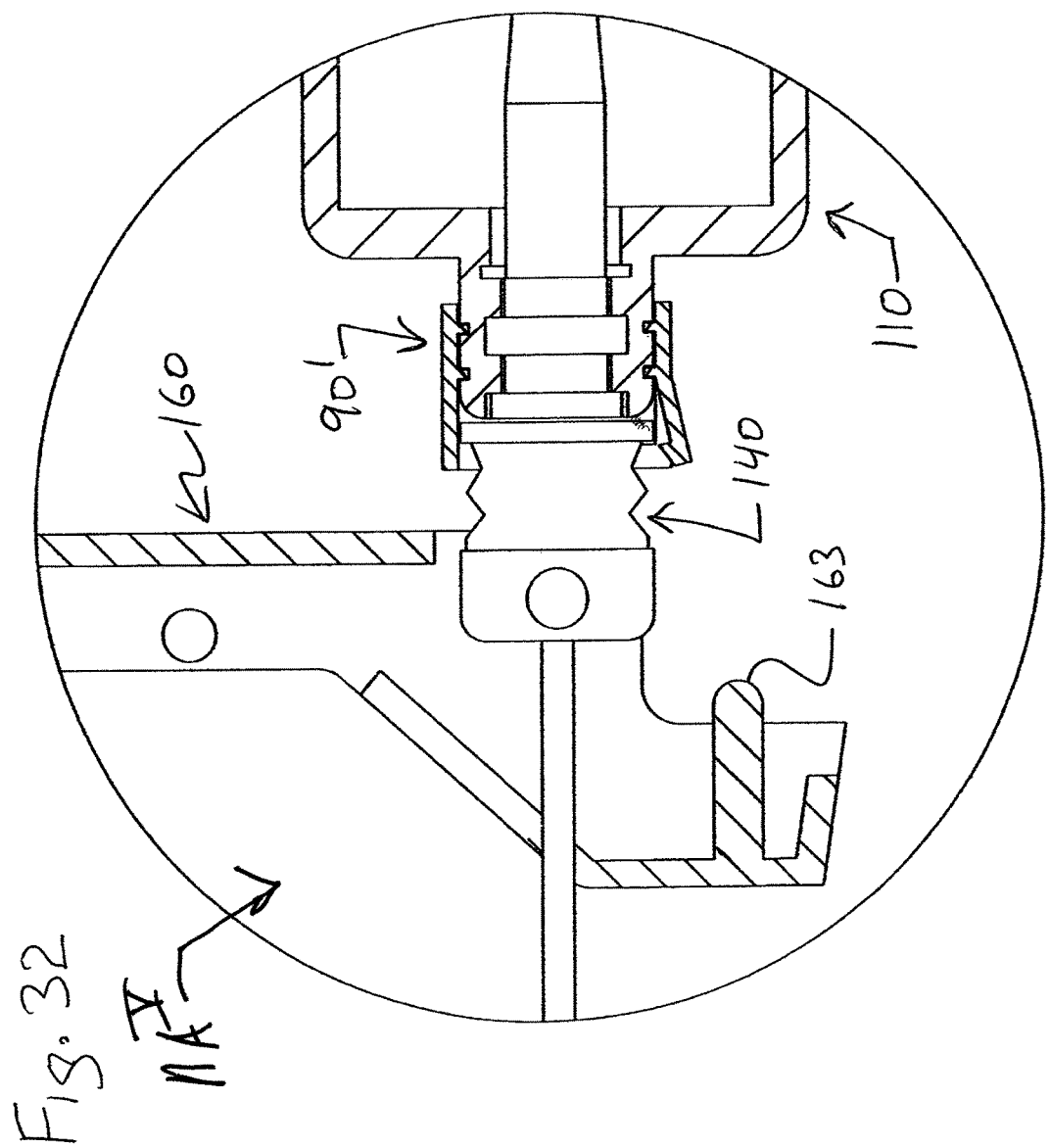
Figure 33:
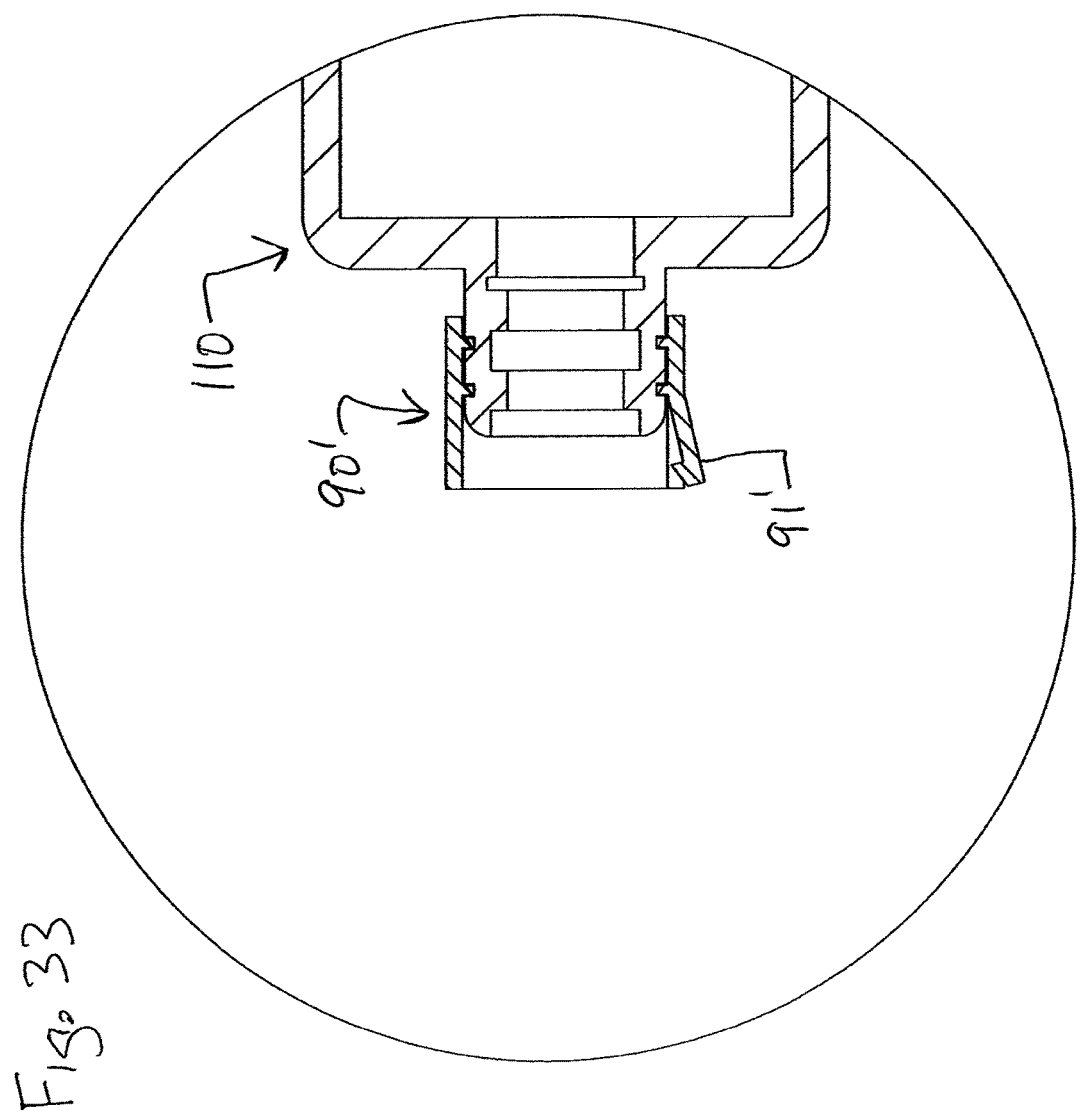
Figure 34:
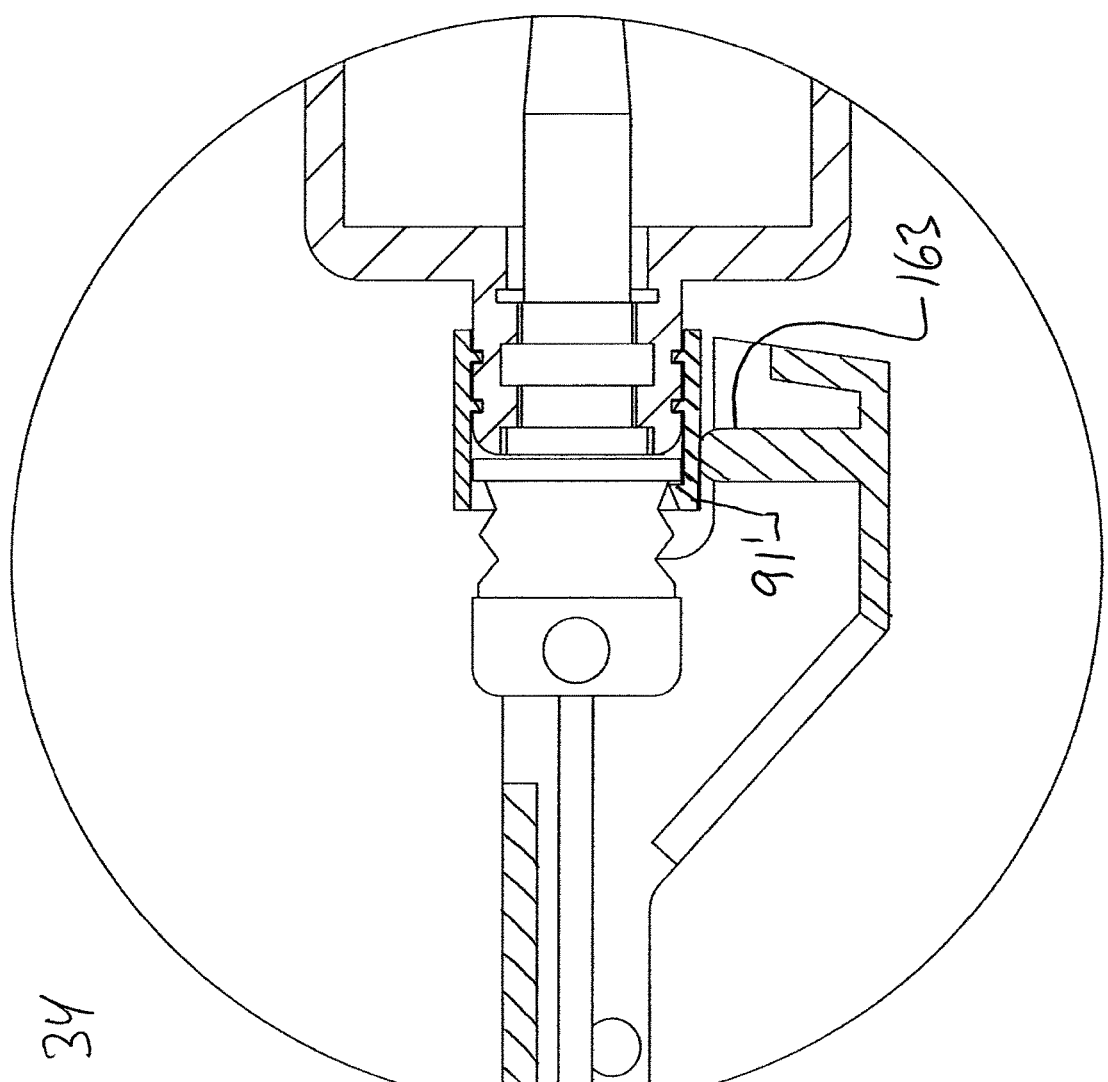

FIGS. 32-34 show various enlarged views of another non-limiting embodiment of the device in accordance with the invention. This embodiment utilizes another embodiment of a needle assembly $NA^V$, which is shown already installed on the device body 110 in FIG. 32. In this embodiment, an activatable locking ring 90' is utilized to prevent removal of the needle assembly $NA^V$ from the body 110 only when the safety cover or needle shield 160 is in the covering position (see FIG. 34). This occurs because a stop projection 163 causes a deflectable finger 91' to move inwardly and engage with a flange of the needle member 140. While in contact therewith, the projection 163/finger 91' prevent removal of the needle assembly $NA^V$ from the device body 110. Once the needle assembly $NA^V$ is installed (e.g., it can be installed in the same as that of FIGS. 29-31), it can be removed by unthreading it from the body 110. On the other hand, after use of the device, the safety cover 160 can be moved to the covering position shown in FIG. 34, and, when locked therein, prevents (via projection 163 engaging with finger 91') the needle assembly $NA^V$ from being removed. At this point, the entire device can, should and/or must be discarded as a unit.

The devices described herein can also utilize one or more features disclosed in the prior art documents expressly incorporated by reference herein. Furthermore, one or more of the various parts of the device can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any or all disclosed features of one embodiment may be used on any one or all other disclosed embodiments to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A fluid collection/injection device comprising:
a body having a front end, a back end, and a main hollow section arranged between the front and back ends;
a needle hub securing section arranged on the front end and being structured and arranged to receive therein a needle member;
the fluid collection/injection device is structured and arranged to utilize at least an installation mode, an operational mode, and a post-use mode;
in the installation mode, the needle member being coupled to the body via the needle hub securing section;
in the operational mode, fluid passing through the needle member and into or out of a receptacle inserted into the main hollow section; and
in the post-use mode, a safety cover at least one of:
prevents removal of the needle member from the fluid collection/injection device;
prevents removal of the needle member from the needle hub securing section;
activates release of the needle member from the body such that when the safety cover is in a position covering a needle of the needle member, the needle member can fall out of the needle hub securing section;
activates release of the needle member from the body such that when the safety cover is in a position covering a needle of the needle member, the needle member is no longer securely retained to the needle hub securing section;
releases a securing engagement between the needle member and the needle hub securing section;
unlocks a locking connection between the needle member and the needle hub securing section; and
moves a mechanism arranged in an area of the needle hub securing section which releases a connection between the needle member and the needle hub securing section.

2. The device of claim 1, wherein the body is one of generally cylindrical and generally tubular.

3. The device of claim 1, wherein the needle hub securing section comprises a fixed part and a movable part.

4. The device of claim 3, wherein the fixed part is integrally formed with the front end and the movable part is arranged on a member that has one end which is one of:
fixed to a portion of the main hollow section;
connected to a portion of the main hollow section via a living hinge;
removably connected to a portion of the main hollow section; and
integrally formed with the main hollow section.

5. The device of claim 4, wherein the fixed part and the movable part each generally comprise one-half of an internal locking thread structured and arranged to engage with an external thread of the needle member.

6. The device of claim 4, wherein the member has one end which is fixed to the portion of the main hollow section.

7. The device of claim 4, wherein the member has one end which is removably connected to the portion of the main hollow section.

8. The device of claim 4, wherein the member has one end which is integrally formed with the main hollow section.

9. The device of claim 4, wherein the member has one end which is connected to the portion of the main hollow section via the living hinge.

10. The device of claim 1, wherein the safety cover is at least one of:
pivotally mounted or connected to a portion of the needle member;
movably mounted to a portion of the needle member;
movable from a position not covering a proximal needle of the needle member to a position covering the proximal needle; and
movable from an initial position to a locking position covering the proximal needle.

11. The device of claim 1, wherein the body is a one-piece member.

12. The device of claim 1, further comprising guide projections arranged on the front end of the body.

13. The device of claim 1, wherein the front end comprises a through opening sized to receive an inner needle end of the needle member.

14. The device of claim 1, wherein the rear end comprises a flange.

15. The device of claim 1, further comprising a locking mechanism that prevents the needle member from being reinstalled on the body.

16. The device of claim 1, further comprising a mechanism for preventing re-use of the device.

17. The device of claim 1, further comprising a mechanism for rendering the device single-use.

18. A method of taking a fluid sample using the device of claim 1, the method comprising:
installing the needle member;
inserting a receptacle into the device;
removing the receptacle from the device; and
moving a safety cover to a needle covering position after use.

19. A method of taking a fluid sample using the device of claim 1, the method comprising:
inserting a receptacle into the body;
removing the receptacle from the body; and
moving a safety cover to a needle covering position.

20. A method of taking a fluid sample using the device of claim 1, the method comprising:
inserting a receptacle into the main hollow section;
removing the receptacle; and
preventing re-use of the device.

21. A fluid collection device comprising:
a body having a front end, a back end, and a main hollow section arranged between the front and back ends;
a needle hub securing section arranged on the front end and being structured and arranged to receive therein a needle member;
the fluid collection device is structured and arranged to utilize at least an installation mode, an operational mode, and a post-use mode;
in the installation mode, the needle member being coupled to the body via the needle hub securing section;
in the operational mode, fluid passing through the needle member and into a receptacle inserted into the main hollow section; and
in the post-use mode, a safety cover at least one of:
prevents removal of the needle member from the fluid collection device;
prevents removal of the needle member from the needle hub securing section;
activates release of the needle member from the body such that when the safety cover is in a position covering a needle of the needle member, the needle member can fall out of the needle hub securing section;
activates release of the needle member from the body such that when the safety cover is in a position covering a needle of the needle member, the needle member is no longer securely retained to the needle hub securing section;
releases a securing engagement between the needle member and the needle hub securing section;
unlocks a locking connection between the needle member and the needle hub securing section; and
moves a mechanism arranged in an area of the needle hub securing section which releases a connection between the needle member and the needle hub securing section.

22. A needle assembly structured and arranged for use on a fluid collection device comprising a body having a front end, a back end, and a main hollow section arranged between the front and back ends, a needle hub securing section arranged on the front end and being structured and arranged to receive therein the needle assembly, the needle assembly being configured to operate in at least an installation mode, an operational mode, and a post-use mode;
in the installation mode, the needle assembly being coupled to the body via the needle hub securing section;
in the operational mode, fluid passing through a needle of the needle assembly into or out of a receptacle inserted into the main hollow section; and
in the post-use mode, a safety cover of the needle assembly at least one of:
prevents removal of the needle member from the needle assembly;
prevents removal of the needle member from the needle hub securing section;
activates release of the needle member from the body such that when the safety cover is in a position covering a needle of the needle member, the needle member can fall out of the needle hub securing section;
activates release of the needle member from the body such that when the safety cover is in a position covering a needle of the needle member, the needle member is no longer securely retained to the needle hub securing section;
releases a securing engagement between the needle member and the needle hub securing section;
unlocks a locking connection between the needle member and the needle hub securing section; and
moves a mechanism arranged in an area of the needle hub securing section which releases a connection between the needle member and the needle hub securing section.

* * * * *